(12) United States Patent
Miller et al.

(10) Patent No.: US 7,899,528 B2
(45) Date of Patent: Mar. 1, 2011

(54) METHOD AND APPARATUS TO MONITOR PATIENTS AND TREAT WITH INTRAOSSEOUS FLUIDS

(75) Inventors: Larry J. Miller, Spring Branch, TX (US); David S. Bolleter, San Antonio, TX (US); Robert W. Titkemeyer, San Antonio, TX (US)

(73) Assignee: Vidacare Corporation, Shavano Park, TX (US)

( * ) Notice: Subject to any disclaimer, the term of this patent is extended or adjusted under 35 U.S.C. 154(b) by 209 days.

(21) Appl. No.: 12/120,992

(22) Filed: May 15, 2008

(65) Prior Publication Data

US 2008/0287859 A1 Nov. 20, 2008

Related U.S. Application Data

(60) Provisional application No. 60/938,501, filed on May 17, 2007.

(51) Int. Cl.
*A61N 1/39* (2006.01)
(52) U.S. Cl. .................................. 607/3; 607/5
(58) Field of Classification Search .................. 607/3, 5, 607/2; 600/508, 509
See application file for complete search history.

(56) References Cited

U.S. PATENT DOCUMENTS

| | | | |
|---|---|---|---|
| 3,104,448 A | 9/1963 | Morrow et al. | 27/24 |
| 3,835,860 A | 9/1974 | Garretson | 128/310 |
| 4,021,920 A | 5/1977 | Kirschner et al. | 32/28 |
| 4,185,619 A | 1/1980 | Reiss | 128/1.1 |
| 4,194,505 A | 3/1980 | Schmitz | 128/218 |
| 4,333,459 A | 6/1982 | Becker | 128/218 F |
| 4,692,073 A | 9/1987 | Martindell | 408/239 A |
| 4,713,061 A | 12/1987 | Tarello et al. | 604/200 |
| 4,787,893 A | 11/1988 | Villette | 604/188 |
| 4,793,363 A | 12/1988 | Ausherman et al. | 128/754 |
| 4,969,870 A | 11/1990 | Kramer et al. | 604/51 |
| 5,002,546 A | 3/1991 | Romano | 606/80 |

(Continued)

FOREIGN PATENT DOCUMENTS

FR 2457105 12/1980

(Continued)

OTHER PUBLICATIONS

International Search Report and Written Opinion; PCT/US08/63688; pp. 10, Dec. 1, 2008.

(Continued)

*Primary Examiner* — Carl H Layno
*Assistant Examiner* — Brian T Gedeon
(74) *Attorney, Agent, or Firm* — Baker Botts L.L.P.

(57) ABSTRACT

Automatic external defibrillator apparatus may be provided for use in cooperation with an intraosseous apparatus. Apparatus and methods may also be provided to execute protocols calling for external defibrillation and drug delivery. The disclosure provides a medical apparatus including two electrodes, a processor, a display, a driver, a drug delivery slot, a drug delivery port, and a voltage source. The two electrodes may include an attachment operable to releasably connect the two electrodes to the patient. The processor may be operable to collect and analyze a rhythm associated with the patient's heart from the two electrodes. The display may be operable to communicate instructions to a user. The driver may be operable to insert an intraosseous device into a bone and associated bone marrow of the patient. The drug delivery slot may be operable to receive a drug. The drug delivery port may be operable to communicate the drug from the drug delivery slot to the patient via the intraosseous device. The voltage source may be operable to deliver an electric shock to the patient via the two electrodes.

21 Claims, 14 Drawing Sheets

U.S. PATENT DOCUMENTS

| | | | |
|---|---|---|---|
| 5,324,300 A | 6/1994 | Elias et al. | 606/180 |
| RE34,800 E | 11/1994 | Hutchins | 128/898 |
| 5,405,362 A | 4/1995 | Kramer et al. | 607/5 |
| 5,529,580 A | 6/1996 | Kusunoki | 606/170 |
| 5,586,847 A | 12/1996 | Mattern, Jr. et al. | 408/239 A |
| 5,595,186 A | 1/1997 | Rubinstein et al. | 128/574 |
| 5,645,571 A | 7/1997 | Olson et al. | 607/5 |
| 5,724,873 A | 3/1998 | Hillinger | 81/451 |
| 5,797,969 A | 8/1998 | Olson et al. | 607/5 |
| 5,799,682 A | 9/1998 | Wu et al. | 139/383 AA |
| 5,913,685 A | 6/1999 | Hutchins | 434/265 |
| 5,924,864 A | 7/1999 | Loge et al. | 433/118 |
| 5,960,797 A | 10/1999 | Kramer et al. | 128/899 |
| 5,980,545 A | 11/1999 | Pacala et al. | 606/170 |
| 6,047,212 A | 4/2000 | Gliner et al. | 607/7 |
| 6,102,915 A | 8/2000 | Bresler et al. | 606/80 |
| 6,210,376 B1 | 4/2001 | Grayson | 604/264 |
| 6,356,785 B1 | 3/2002 | Snyder et al. | 607/5 |
| 6,547,561 B2 | 4/2003 | Meller et al. | 433/80 |
| 6,626,173 B2 | 9/2003 | Genova et al. | 128/203.15 |
| 6,761,726 B1 | 7/2004 | Findlay et al. | 606/182 |
| 7,011,528 B2 | 3/2006 | Tweet et al. | 434/262 |
| 7,192,284 B2 | 3/2007 | Eggert et al. | 434/268 |
| 7,299,087 B2 | 11/2007 | Bardy | 600/513 |
| 2006/0281724 A1 | 12/2006 | Loria | 514/178 |
| 2007/0084742 A1 | 4/2007 | Miller et al. | 206/438 |

FOREIGN PATENT DOCUMENTS

FR          2516386          5/1983

OTHER PUBLICATIONS

International Preliminary Report on Patentability; PCT/US08/63688; pp. 8, Nov. 26, 2009.

Official Action, European Application No. 08769475.8, 2 pages, May 18, 2010.

European Extended Search Report, Application No. 08769475.8, 8 pages, Sep. 29, 2010.

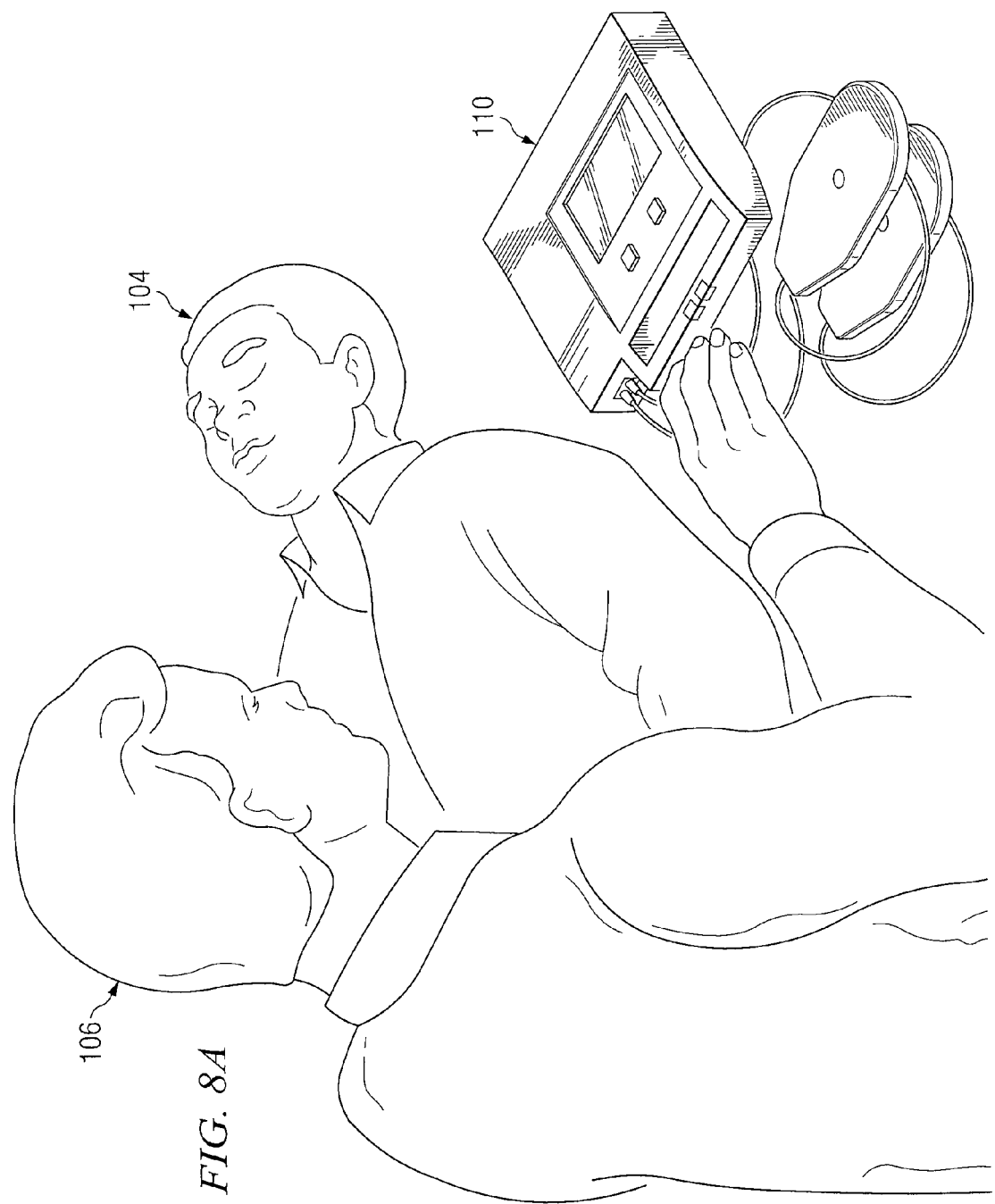

METHOD AND APPARATUS TO MONITOR PATIENTS AND TREAT WITH INTRAOSSEOUS FLUIDS

RELATED APPLICATION

This application claims the benefit of provisional patent application entitled "SMART PARAMEDIC," Provisional Application Ser. No. 60/938,501 filed May 17, 2007. The contents of this application is incorporated herein in its entirety by this reference.

TECHNICAL FIELD

The present disclosure is related to apparatus and methods which may be used to communicate fluids with a patient's vascular system via an intraosseous device in cooperation with an automatic external defibrillator.

BACKGROUND OF THE DISCLOSURE

Automatic external defibrillators (AEDs) are increasingly common due to concerted campaigns to equip locations with large numbers of people, such as airports, schools, churches, office building, and/or other gathering locations. In addition, trained first responders are often equipped with AED kits. It is asserted that treatment with an AED significantly increases a patient's chances of survival in the event of cardiac arrhythmia.

According to the Federal Food and Drug Administration, an AED typically comprises adhesive electrode pads for connection with a patient, a microprocessor for collecting and analyzing the rhythms associated with a patient's heart, and a source of voltage operable to deliver a shock through the electrodes in an attempt to correct an arrhythmia. Some AED kits are more properly called semi-automatic, as they require users to press a button or other actuator in response to instructions by the AED itself.

In most cases, an AED includes basic instructions for use in the event a first aid provider is unfamiliar with the equipment. Such instructions may include pictures or text indicating proper attachment of the electrodes and/or operation of the electronics in the kit. Some AEDs, once activated, operate independently by delivering any appropriate shock without further action by the user.

Those patient conditions treated with external defibrillation are often better treated with a combination of defibrillation and drug administration. For instance, Advanced Cardiac Life Support (ACLS) protocol promulgated in the United States by the American Heart Association (AHA) provides a treatment protocol for cardiac conditions. The ACLS protocol may include external defibrillation, administration of drugs, and/or insertion of airway devices.

ACLS protocol may include delivery of any drug or medication, including, but not limited to, calcium, atropine, adenosine, amiodanone, epinephrine, bicarb, versed, and/or lidocaine. Delivery of drugs during the course of ACLS protocol may include repeated injections and/or installing a IV connection.

SUMMARY OF THE DISCLOSURE

In accordance with teachings of the present disclosure, apparatus and methods may be provided to facilitate access to a patient's vascular system and to communicate fluids with the vascular system. These teachings may provide increased effectiveness in treatment of a patient in accord with an Automatic External Defibrillator.

Apparatus and methods incorporating teachings of the present disclosure may be used to treat various patient conditions including, but not limited to, cardiac arrest, ventricular fibrillation, pulseless ventricular tachycardia, bradycardia and/or any other sort of cardiac arrhythmia. Installation of an IO device may offer improved access, increased fluid flow rates and numerous other benefits over IV fluid delivery or repeated injections.

One aspect of the present disclosure may include providing apparatus and methods for treating a patient including operating an automatic external defibrillator in cooperation with insertion of an intraosseous device disposed in a bone and associated bone marrow. Structures, apparatus and techniques incorporating teachings of the present disclosure may be used with a wide variety of intraosseous devices.

Teachings of the present disclosure may be useful to establish vascular access during treatment at a wide variety of acute and chronic conditions at locations and facilities including, but not limited to, accident sites, emergency rooms, battlefields, emergency medical services (EMS) facilities, oncology treatment centers, and chronic disease treatment facilities. Various teachings of the present disclosure may be used during treatment of animals in a veterinary practice.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIGS. 8A and 8B are drawings showing one embodiment incorporating a method of operating an automatic external defibrillator in accordance with teachings of the present disclosure;

DETAILED DESCRIPTION OF THE DISCLOSURE

Figure 1:
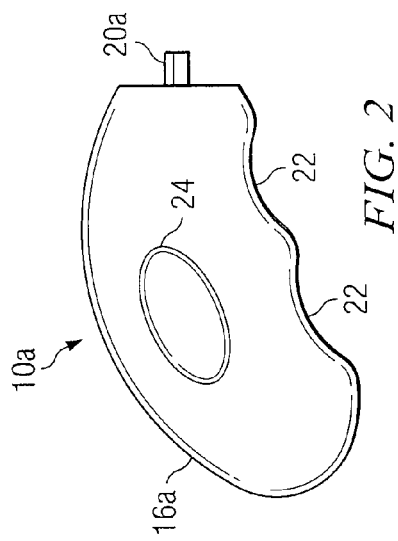
FIG. 1 is a schematic drawing showing an isometric view of a powered driver which may be used to place an intraosseous device at a selected insertion site.

Preferred embodiments of the disclosure and its advantages are best understood by reference to FIGS. 1-15 wherein like numbers refer to same and like parts.

Vascular access is often essential to viability of a patient in emergency situations, during transportation to a medical facility and during treatment at the medical facility. Obtaining vascular access may be a significant problem in five to ten percent of patients of all ages and weights in pre-hospital and hospital environments. This equates to approximately six (6) million patients in the U.S. annually. For example patients suffering from conditions such as shock, cardiac arrest, drug overdose, dehydration, diabetic coma, renal failure and altered states of consciousness may have very few (if any) accessible veins.

In a hospital or similar medical facility, central line access is often an alternative to IV access. However, central line access generally takes longer, costs more, may have a higher risk of complications and requires skilled personnel to properly insert the central line. In many hospital environments, nurses and physicians are increasingly turning to intraosseous (IO) access as an alternative to IV access, rather than central lines. In pre-hospital environments, paramedics and other emergency medical service (EMS) providers are often finding that IO access may be quick, safe and effective when IV placement is challenging.

Intraosseous (IO) access to bone and associated bone marrow has been used for other procedures including, but not limited to, obtaining biopsy specimens for analysis and research and also for bone marrow transplantation and/or stem cell research.

Persons having ordinary skill in the art and practicing the teachings of this disclosure may be able to combine the benefits of an automatic external defibrillator (AED) with an IO installation kit and drug delivery. For example, a combination device may provide automatic or semi-automatic delivery of defibrillating shock and IO drugs as identified by the ACLS protocol. In such cases, the combination device may include all the features of an AED as discussed in detail above as well as instructions to users regarding installation of an IO device and automatic or semi-automatic delivery of drugs as promulgated in the ACLS protocol.

Teachings of the present disclosure may be satisfactorily used to communicate fluids with the intraosseous device at a wide variety of locations. For example, apparatus and methods incorporating teachings of the present invention may be used to provide intraosseous access to a patient's vascular system in the sternum, the proximal humerus (the shoulder area), the proximal tibia (below the knee), and the distal tibia (above the inside of the ankle). Teachings of the present disclosure are not, however, limited to IO devices which may be inserted at the tibia, humerus, or sternum.

The upper tibia proximate a patient's knee or the humeral head proximate a patient's shoulder may be used as insertion sites for an IO device to establish access with the patient's vascular system. Sternal access may also be used as an insertion site. Availability of multiple intraosseous sites has proven to be especially important in applications such as emergency treatment of battlefield casualties or other mass casualty situation. Teachings of the present disclosure may be used at a wide variety of insertion sites.

The distal tibia is located just above the inside of the ankle. This location may more readily provide vascular access to morbidly obese patients. The distal tibia is usually a thinner area of the body. Using the distal tibia as an insertion site may allow emergency medical service personnel to pump medications and fluids into the body of obese patients when regular conventional IV access is difficult. EMS personnel may often not be able to start conventional IV infusions in obese patients because their size may obscure many of the veins used for conventional access. Adipose tissue (fat) around other available IO access sites may be so thick that EMS personnel cannot reach the bone and associated bone marrow with available IO needles. In such cases, disposition of an IO needle in the distal tibia may offer a significant improvement in vascular access to the overweight population.

The humeral head and sternum further provide insertion sites for an intraosseous device located above the diaphragm of a patient. Placing or inserting an intraosseous device above the diaphragm may be preferred by some emergency room physicians and trauma surgeons for rapid vascular access.

Intraosseous access may also be used as a "routine" procedure with chronic conditions which substantially reduce or eliminate the availability of conventional IV sites. Examples of such chronic conditions may include, but are not limited to, dialysis patients, seriously ill patients in intensive care units and epilepsy patients. Intraosseous devices along with supporting structure and/or monitoring equipment incorporating teachings of the present disclosure may be quickly and safely used to provide IO access to a patient's vascular system in difficult cases such as status epilepticus to give medical personnel an opportunity to administer crucial medications and/or fluids. Further examples of such acute and chronic conditions are listed near the end of this written description. Insertion sites and associated target areas for IO placement such as a patient's tibia, humerus, or sternum are often larger than insertion sites and associated target areas for placement of an IV device making IO insertion easier than IV insertion.

The term "driver" may be used in this application to include any type of powered driver or manual driver satisfactory for installing an intraosseous (IO) device such as a penetrator assembly or an IO needle into a selected target site.

For some applications a powered driver or a manual driver may be directly coupled with an IO device. For other applications various types of connectors may be used to couple a manual driver or a powered driver with an IO device. A wide variety of connectors and associated connector receptacles, fittings and/or other types of connections with various dimensions and configurations may be satisfactorily used to releasably engage an IO device with a powered driver or a manual driver.

The term "intraosseous (IO) device" may be used in this application to include any hollow needle, hollow drill bit, penetrator assembly, bone penetrator, catheter, cannula, trocar, inner penetrator, outer penetrator, IO needle or IO needle set operable to provide access to an intraosseous space or interior portions of a bone. A wide variety of trocars, spindles and/or shafts may be disposed within a cannula during installation at a selected target area. Such trocars, spindles and shafts may also be characterized as inner penetrators. A cannula may be characterized as an outer penetrator.

The term "fluid" may be used within this patent application to include any liquid including, but not limited to, blood, water, saline solutions, IV solutions, plasma or any mixture of liquids, particulate matter, dissolved medication and/or drugs appropriate for injection into bone marrow or other target sites. The term "fluid" may also be used within this patent application to include body fluids such as, but not limited to, blood, bone marrow and cells which may be withdrawn from a target site.

Various features of the present disclosure may be described with respect to powered driver 10 and/or manual driver 10a. Various features of the present disclosure may also be described with respect to intraosseous device-hub 60. However, intraosseous fluid delivery systems incorporating teachings of the present disclosure may be satisfactorily used with a wide variety of drivers and intraosseous devices. The present disclosure is not limited to use with intraosseous device-hub 60 or drivers 10 or 10a.

FIG. 1 shows an embodiment of a powered driver 10 which may be satisfactorily used to insert an intraosseous device into a selected target area or penetration site. Powered driver 10 may include housing 12 with various types of motors and/or gear assemblies disposed therein (not expressly shown). A rotatable shaft (not expressly shown) may be disposed within housing 12 and connected with a gear assembly (not expressly shown). Various types of fittings, connections, connectors and/or connector receptacles may be provided at one end of the rotatable shaft extending from end 14 of housing 12.

For some applications pin type fitting or connector 20 may be formed on the one end of the rotatable shaft. A matching box type fitting or connector receptacle may be provided on an intraosseous device so that connector 20 of powered driver 10 may be releasably engaged with the intraosseous device. For some applications, connector 20 may have a pentagonal shaped cross section with tapered surfaces formed on the exterior thereof.

Handle 16 may include a battery (not expressly shown) or other power source. Handle 16 may also include trigger assembly 18 for use in activating powered driver 10. Examples of powered drivers are shown in pending patent applications Ser. No. 10/449,503 filed May 30, 2003 entitled "Apparatus and Method to Provide Emergency Access To Bone Marrow," now U.S. Pat. No. 7,670,328; Ser. No. 10/449,476 filed May 30, 2003 entitled "Apparatus and Method to Access Bone Marrow," now U.S. Pat. No. 7,699,850; and Ser. No. 11/042,912 filed Jan. 25, 2005 entitled "Manual Intraosseous Device."

Figure 2:
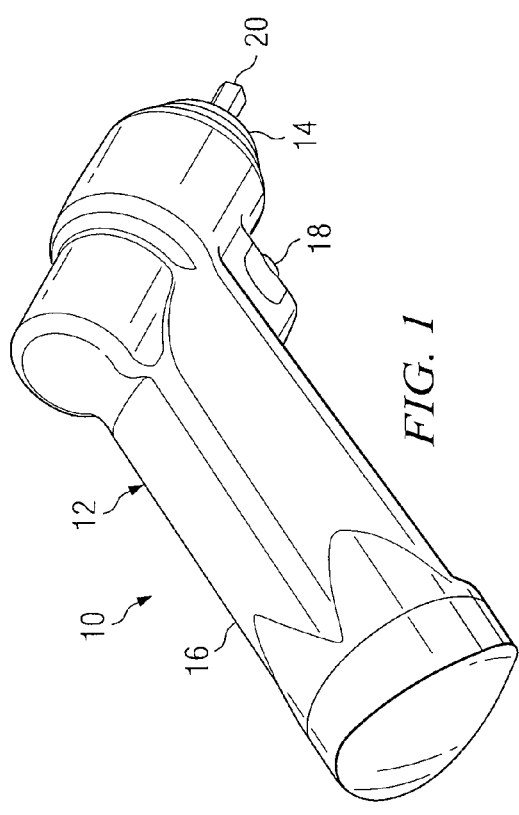
FIG. 2 is a schematic drawing showing a side view of a manual driver which may be used to place an intraosseous device at a selected insertion site.

FIG. 2 shows one example of a manual driver which may be satisfactorily used to insert an intraosseous device into a selected target area. For this embodiment manual driver 10a may be generally described as having handle 16a with a "pistol grip" configuration. Handle 16a has an ergonomic design with finger grips 22 and one or more finger rests 24.

Connector 20a may extend from first end 14a of handle 16a. Connector 20a may have a configuration and dimensions similar to previously described connector 20. However, manual drivers may be provided with a wide variety of connectors and/or connector receptacles. Various details concerning manual drivers are discussed in more detail in pending U.S. patent application Ser. No. 11/042,912 filed Jan. 25, 2005, entitled "Manual Intraosseous Driver."

Figure 3:
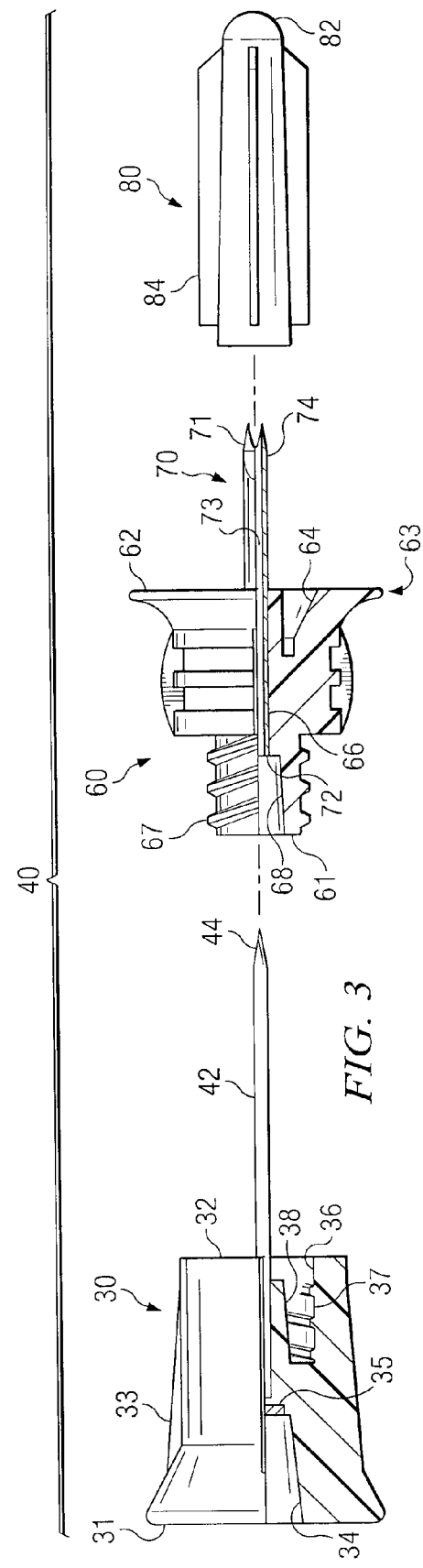
FIG. 3 is a schematic drawing in section and in elevation with portions broken away showing an exploded view of one example of an intraosseous device.

FIG. 3 is a schematic drawing showing an exploded view of one example of a penetrator assembly which may be used to provide access to a patient's vascular system. Penetrator assembly or IO needle set 40 may include connector 30, hub 60 and cover 80. Connector 30 may be described as having a generally cylindrical configuration defined in part by first end 31 and second end 32.

First end 31 may include opening 34 formed with various configurations and/or dimensions. For some applications opening 34 may be sized to receive portions of a drive shaft. One or more webs (not expressly shown) may also be formed in first end 31 extending from opening 34. Open segments or void spaces (not expressly shown) may be formed between such webs. Opening 34 and associated webs (if any) may be used to releasably engage connector 30 with either a manual driver or a powered driver.

The configuration and dimensions of opening 34 may be selected to be compatible with releasably engaging connector 30 of IO needle set 40 to connector 20 of powered driver 10 or connector 20a of manual driver 10a. For some applications metallic disk 35 may be disposed within opening 34 for use in releasably engaging needle set 40 to a magnet (not expressly shown) disposed on the end of connector 20 or 20a.

For some applications exterior portion of connector 30 may include an enlarged tapered portion adjacent to first end 31. A plurality of longitudinal ridges 33 may also be formed on the exterior of connector 30 proximate first end 31. The enlarged tapered portion and/or longitudinal ridges 33 may allow an operator to grasp associated IO needle set 40 during attachment with a driver and may facilitate disengagement of connector 30 from hub 60 after outer penetrator or cannula 70 has been inserted into a bone and associated bone marrow.

Second opening 36 may be formed in second end 32 of connector 30. The configuration and dimensions of opening 36 may be selected to be compatible with releasably engaging the relevant portion of hub 60. For example threads 37 may be formed on interior portions of opening 36 extending from second end 32. Threads 37 may be sized to engage threads 67 formed on an exterior portion of hub 60. In addition, opening 36 may include male luer slip 38, configured to correspond to female luer slip 68 in hub 60. It should be noted that male luer slip 38 and female luer slip 68 do not come into physical contact when connector 30 and hub 60 are connected. Threads 37 and 67 may be characterized as forming portions of a Luer lock connection. However, the present disclosure is not limited to threads 37 and 67. Various types of releasable connections including, but not limited to, other types of locking connections may be formed on adjacent portions of connector 30 and hub 60.

Trocar or inner penetrator 42 may be securely engaged with connector 30 extending from second end 32. The dimensions and configuration of inner penetrator 42 may be selected to allow inner penetrator 42 to be slidably inserted into longitudinal bore 73 of outer penetrator or cannula 70. Trocar 42 may include first end or tip 44. The dimensions and configuration of tip 44 may be selected to accommodate inserting inner penetrator 42 into bone and associated bone marrow at a selected target area in a patient.

Hub 60 may include first end or distal end 61 and second end or proximal end 62. First end 61 may include any features selected to be compatible with connector 30. For example first end 61 of hub 60 may have a generally cylindrical pin-type configuration compatible with releasably engaging hub 60 with second end 32 of connector 30. As another example, hub 60 may include threads 67 formed adjacent to first end 61 of hub 60. Threads 67 may be compatible to be releasably engaged with threads 37 formed on interior portions of opening 36 of connector 30.

For some applications first end 61 of hub 60 may be configured to accommodate various connectors and/or to allow access for various methods of fluid delivery (e.g., a luer lock, a syringe, a standard IV connection and/or a needle). For example, first end 61 of hub 60 may include a check valve (not expressly shown), the check valve operable to allow fluid access via engaged luer lock connections and to restrict fluid access in the absence of an engaged luer lock connector. In another example, first end 61 of hub 60 may include a gasket (not expressly shown) operable to allow fluid access when punctured by a needle and to restrict fluid access in the absence of an engaged needle.

For some applications second end 62 of hub 60 may include flange 63. The dimensions and configuration of second end 62 of hub 60 may be varied to accommodate various insertion sites for an IO device. Hub 60 may be formed with a wide variety of flanges or other configurations compatible with contacting a patient's skin adjacent a desired insertion site.

Passageway 66 may extend from first end 61 through hub 60 to second end 62. Portions of passageway 66 extending from second end 62 may have dimensions selected to be compatible with securely engaging exterior portions of outer penetrator or cannula 70 with hub 60. Second end 72 of cannula 70 may be disposed within passageway 66 between first end 61 and second end 62. First end 71 of cannula 70 may extend from second end 62 of hub 60. Portions of passageway 66 extending from first end 61 of hub 60 may have an enlarged inside diameter to accommodate attachment with various types of fluid connectors.

Cannula or outer penetrator 70 may have longitudinal bore 73 extending from first end 71 to second end 72. Exterior dimensions of trocar or inner penetrator 42 are preferably selected to allow inner penetrator 42 be inserted through outer penetrator 70 with first end 44 of inner penetrator 42 generally aligned with first end 71 of outer penetrator 70 after threads 67 have been engaged with threads 37.

Tip 71 of outer penetrator 70 and/or tip 44 of inner penetrator 42 may be operable to penetrate bone and associated bone marrow. The configuration of tips 71 and 44 may be selected to penetrate a bone, bone marrow and other portions of a patient's body with minimum trauma. For some applications tip 44 of inner penetrator 42 may have a generally trapezoid shape with one or more cutting surfaces.

For some applications tips 71 and 44 may be ground together as a single unit during an associated manufacturing process. Providing a matching fit allows respective tips 71 and 44 to act as a single drilling unit to minimize damage as portions of IO needle set 40 are inserted into a bone and associated bone marrow.

Inner penetrator 42 may sometimes include a longitudinal groove (not expressly shown) that runs along one side of inner penetrator 42 to allow bone chips and/or tissue to exit an insertion site as IO needle set 40 is drilled deeper into an associated bone. Outer penetrator 70 and/or inner penetrator 42 may be formed from various materials including, but not limited to, stainless steel, titanium or any other material having suitable strength and durability to penetrate bone and associated bone marrow. The combination of hub 60 with cannula 70 may sometimes be referred to as an "intraosseous needle." The combination of trocar 42 with cannula 70 may sometimes be referred to as a "penetrator set."

Second end 62 and particularly flange 63 may be used to stabilize hub 60 after insertion into a selected target area of a patient. Second end 32 of connector 30 may be releasably engaged from first end 61 of hub 60 after insertion of outer penetrator 70 into associated bone marrow. The depth of such insertion may be dependent upon the distance between tip 71 of cannula 70 and second end 62 of hub 60. Various types of tubing and/or conduit may then be engaged with threads 67 formed on the exterior of hub 60 proximate first end or pin end 61.

Annular slot or groove 64 may be formed within second end 62 and sized to receive one end of protective cover or needle cap 80. Slot or groove 64 may be used to releasably engage cover 80 with hub 60. For some applications cover 80 may be described as a generally hollow tube having rounded end or closed end 82. Cover 80 may be disposed within annular groove 64 to protect portions of outer penetrator 70 and inner penetrator 42 prior to attachment with a manual driver or a powered driver. Cover 80 may include a plurality of longitudinal ridges 84 formed on the exterior thereof. Longitudinal ridges 84 may cooperate with each other to allow installing and removing cover or needle cap 80 without contaminating portions of an associated penetrator needle or IO device. Cover 80 may be formed from various types of plastics and/or metals.

Figure 4:
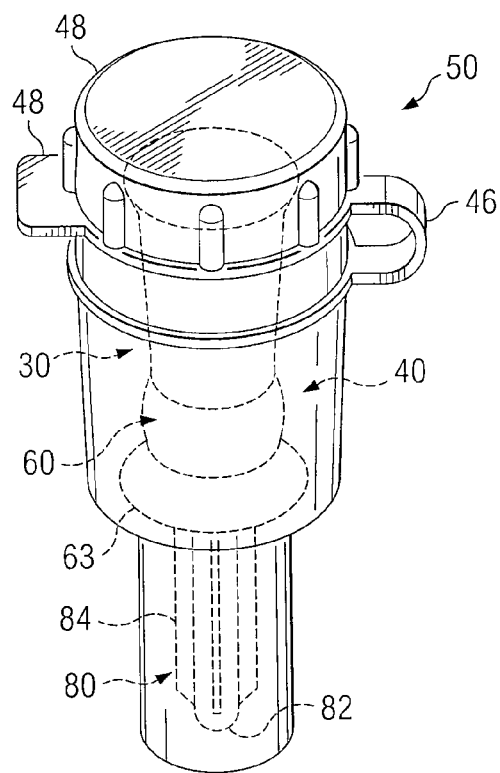
FIG. 4 is a schematic drawing showing an isometric view of the intraosseous device of FIG. 3 disposed in a container.

Canister 50 as shown in FIG. 4 may include lid 48. Lid 48 may be configured to allow lid 48 to be flipped open with one or more digits of an operator's hand. With lid 48 open, an operator may releasably engage a driver with an IO device disposed in container. For example, connector 20 of powered driver 10 may be releasably engaged with connector receptacle 34 of connector 30. Flexible connector 46 may be used to retain lid 48 with canister 50 after lid 48 has been opened.

Figure 5A:
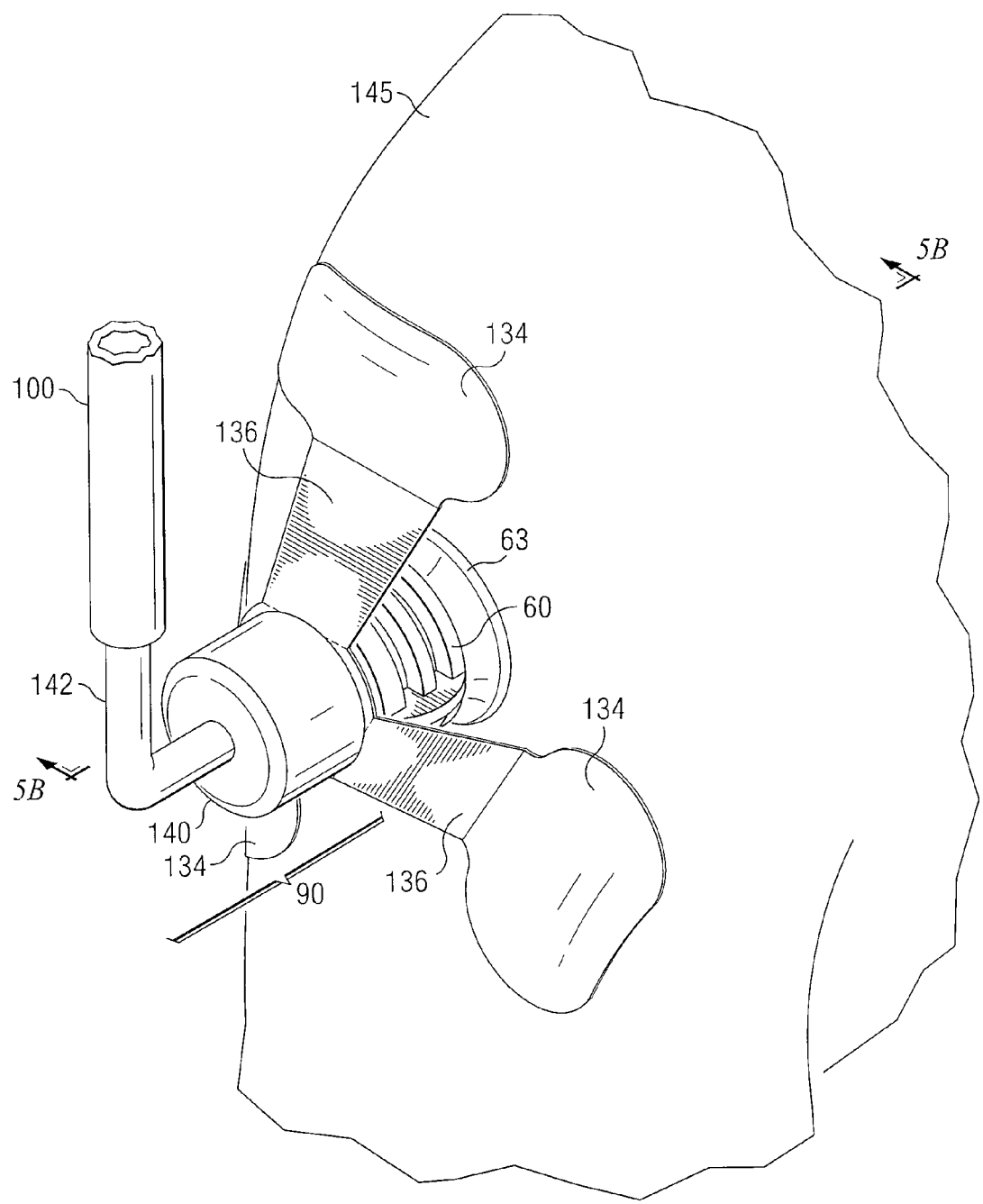
FIG. 5A is a drawing showing an isometric view with portions broken away of a supporting structure and attachment mechanism installed at an insertion site according to one embodiment of the current disclosure.
Figure 5B:
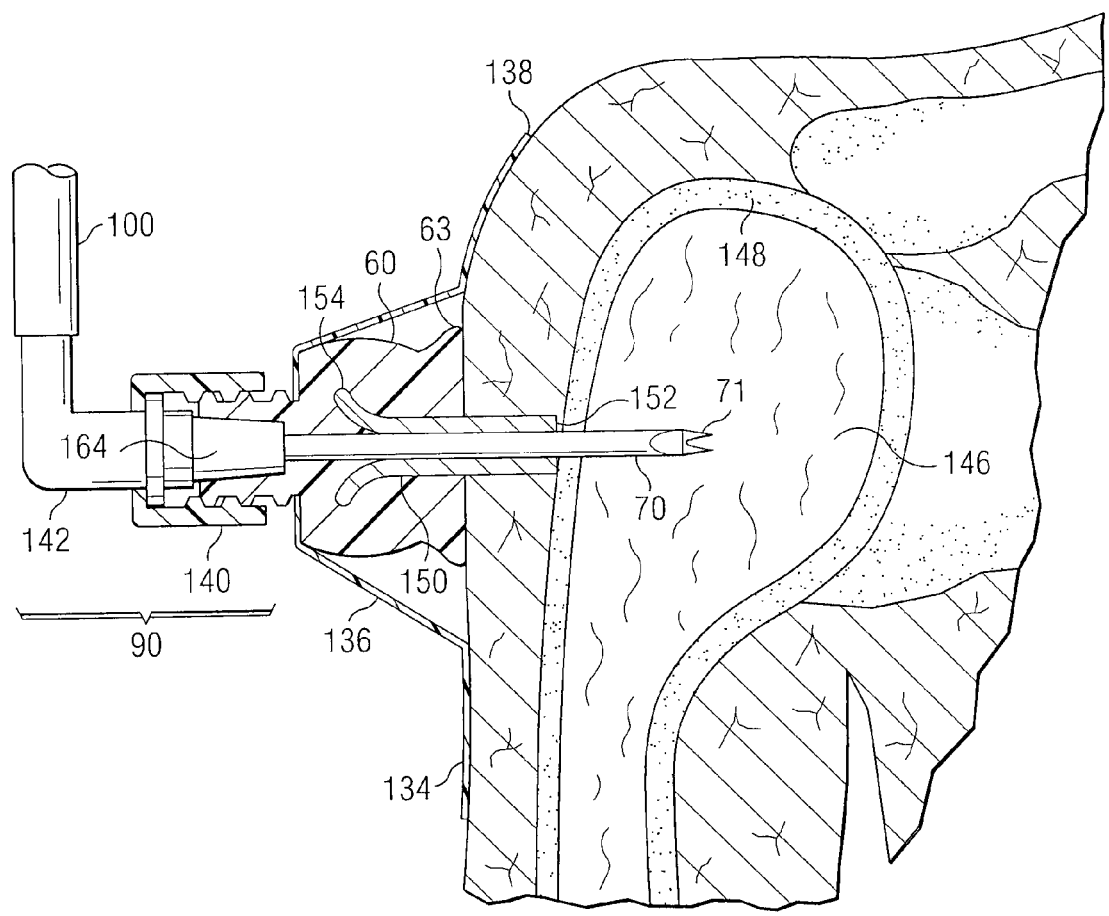
FIG. 5B is a schematic drawing in section taken along line 5B-5B of FIG. 5A showing an intraosseous device inserted into a bone and associated bone marrow along with a supporting structure and attachment mechanism incorporating teachings of the present disclosure.

FIGS. 5A and 5B show an intraosseous device inserted into bone and associated bone marrow along with an attachment mechanism and a support structure incorporating teachings of the present disclosure. Various features of the present disclosure may also be discussed with respect to bone 148 and associated bone marrow 146 as shown in FIGS. 5A and 5B. Bone 148 and bone marrow 146 may be representative of a portion of a patient's upper arm or humeral head, but the teachings of the present disclosure are applicable to any suitable bone or bone marrow.

FIG. 5A shows an isometric view of one embodiment of an intraosseous device located in the humeral end of a patient and stabilized with a support structure. In this embodiment, support structure 130 may include wings 136 and three tabs 134, tabs 134 including adhesive layers 138. Adhesive layers 138 may be disposed against a patient's skin 145 in position to provide stability to hub 60. Wings 136 and tabs 134 may be formed from flexible material operable to conform with exterior portions of hub 60 and/or the configuration of an insertion site.

FIG. 5A also shows connector assembly 90 may include any system or device configured to mate with hub 60 and complete a fluid network with the interior of hub 60. For instance, connector assembly 90 may include luer lock cap 140, right angle connector 142, and flexible tubing 100. In some embodiments, right angle connector 142 may comprise any hollow component configured to complete a fluid network between the interior of hub 60 and an external fluid source and/or receiver such as flexible tubing 100. For instance, right angle connector 142 may include rigid tubing, piping and/or other suitable conduits.

FIG. 5B shows a cross section of the embodiment depicted in FIG. 5A, taken along line 5B-5B. As shown in FIG. 5B, an intraosseous device may be generally described as intraosseous (IO) needle 70 having a hollow, longitudinal bore 73 extending therethrough. First end or tip 71 of IO needle 70 may be designed to drill or cut through bone 148 and penetrate associated bone marrow 146. Tip 71 may be open to allow communication of fluids with bone marrow 146.

Figure 6:
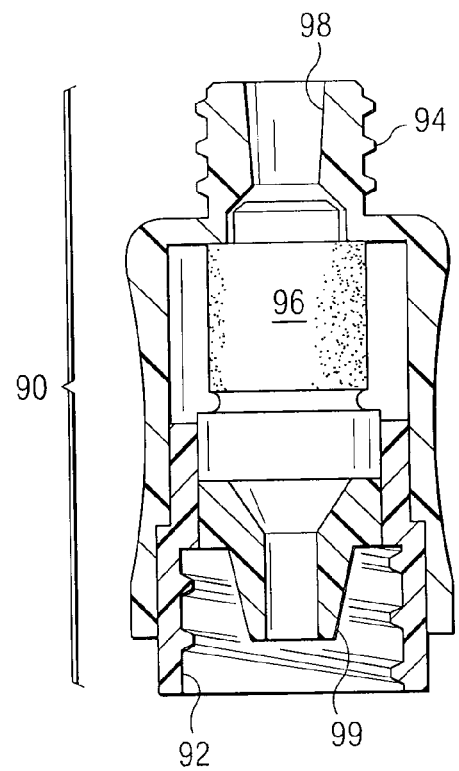
FIG. 6 is a schematic drawing in section showing one example of a connector assembly which may be used to attach a fluid source, pressure pump, and tubing with an intraosseous device in accordance with teachings of the present disclosure.

FIG. 6 shows connector assembly 90 which may be used to communicate fluids with an intraosseous device in accordance with teachings of the present disclosure.

Connector assembly 90 may include any appropriate features or components selected to be compatible with external features of hub 60 or tubing extending therefrom. In some embodiments, such as that shown in FIG. 5A, connector assembly 90 may include internal threads 92 selected to be compatible with threads 67 disposed on hub 60.

Connector assembly 90 may also include any appropriate features or components selected to facilitate attachment to any suitable connections (e.g., extension tubes) for fluid delivery or monitoring devices. For example, connector assembly 90 may include external threads 94 selected to be compatible with a luer lock or other threaded connection.

Connector assembly 90 may include components intended to allow fluid access to hub 60 when appropriate connectors are present. For example, connector assembly may include plug 96. Plug 96 may be any compressible material (e.g., rubber and/or synthetic rubber). In such embodiments, connector assembly 90 may be configured so that plug 96 is under at least some compression in order to create a liquid seal against an inner surface of connector assembly 90. For example connector assembly 90 may include a Halkey-Roberts luer activated valve. One having ordinary skill in the art may recognize additional traditional medical equipment that may be compatible with the IO devices described herein.

Figure 7:
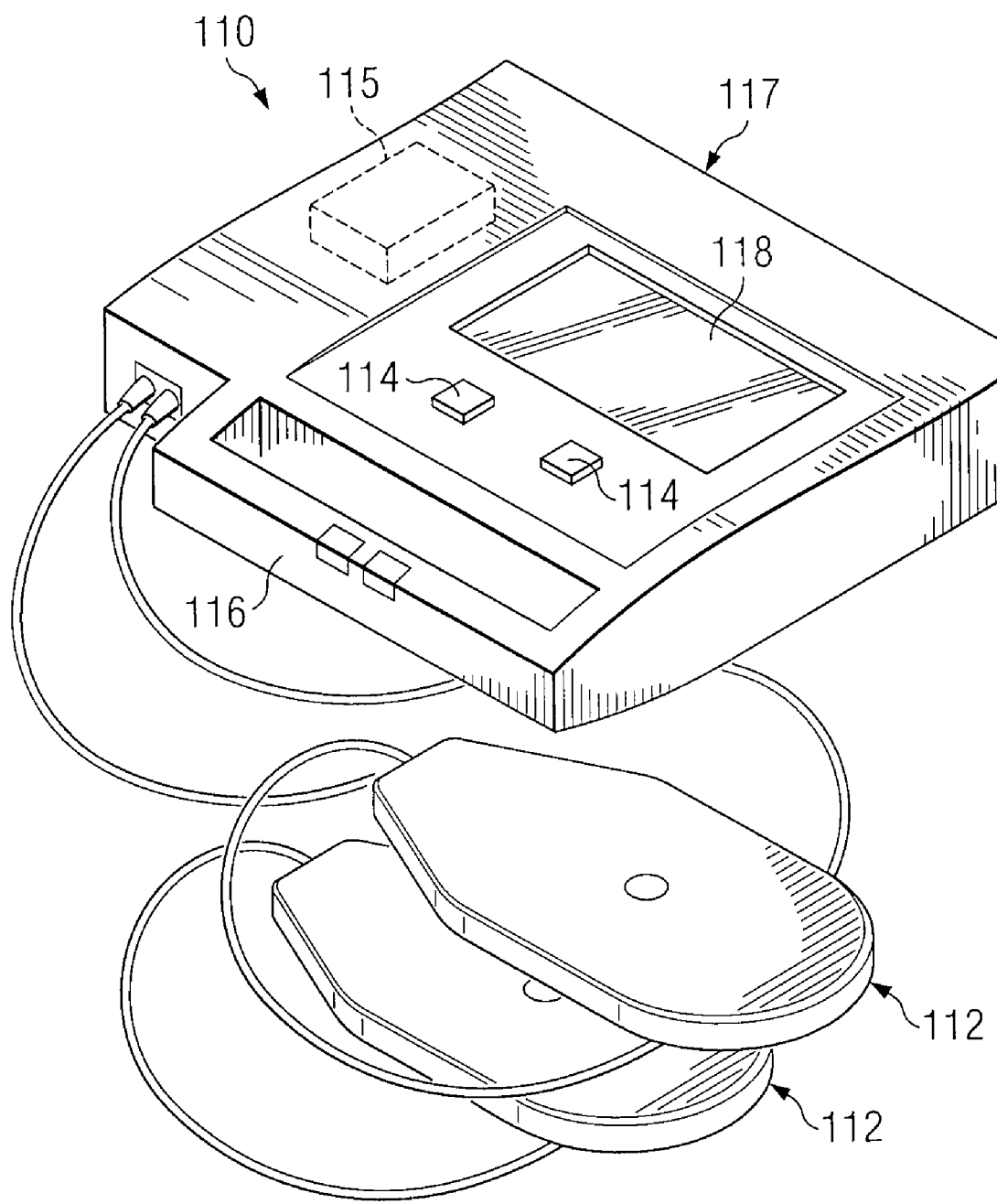
FIG. 7 is a schematic drawing showing one embodiment of an automatic external defibrillator in accordance with teachings of the present disclosure.

FIG. 7 shows Automatic External Defibrillator 110 which may be used to treat a patient exhibiting cardiac arrhythmia in accordance with teachings of the present disclosure. AED 110, as shown in FIG. 7, may include attachable electrodes 112, controls 114, logic processor 115, handle 116 and display 118. AED may be automatic or semi-automatic and may be operable to deliver defibrillating shock under appropriate conditions.

Electrodes 112 may include any suitable means for providing the appropriate connection to patient 104. For example, electrodes 112 may include electrode pads and/or other connectors. Electrodes 112 may be operable to measure a patient's heart rhythms, blood pressure, and/or any other appropriate indicator of patient health.

Controls 114 may include any device configured to allow user 106 to operate AED 110. In embodiments such as that shown in FIG. 7, controls 114 may include depressible buttons. In other embodiments, controls 114 may include any input device (e.g., switches, touchpads, and/or dials).

Logic processor 115 may include any device or devices for processing signals received from electrodes 112 (e.g., converting analog signals to digital signals, and/or interpreting identifiers (e.g., serial numbers, device codes and/or other codes) of various components in AED 110). For example, logic processor 115 may include a device configured to receive a signal generated by electrodes 112, analyze the received signal, and/or convert the signal to a format suitable for communication to user 106. Logic processor 115 may include any suitable hardware or software (e.g., any suitable software, algorithms, or other logic or instructions).

Handle 116 may include any feature of AED 110 that allows user 106 to grasp or manipulate AED 110. In embodiments such as that shown in FIG. 7, handle 116 may include an extension of the shell encasing AED 110 as a whole. In other embodiments, handle 116 may include a strap, an indention of the shell of AED 110, and/or any other physical feature configured to allow user 106 to grasp AED 110.

Display 118 may include any component of AED 110 configured to communicate instructions to user 106. In embodiments such as that shown in FIG. 7, display 118 may include a screen operable to display text commands to user 106. For example, display 118 may include an LCD, a plasma display, a set of LEDs, a segment display, a cathode ray tube, and/or any other useful means of displaying information. Display 118 may be operable to instruct user 106 regarding proper installation of electrodes 112, proper treatment of patient 104, and/or any other information useful in the treatment of patient 104.

Figure 8B:
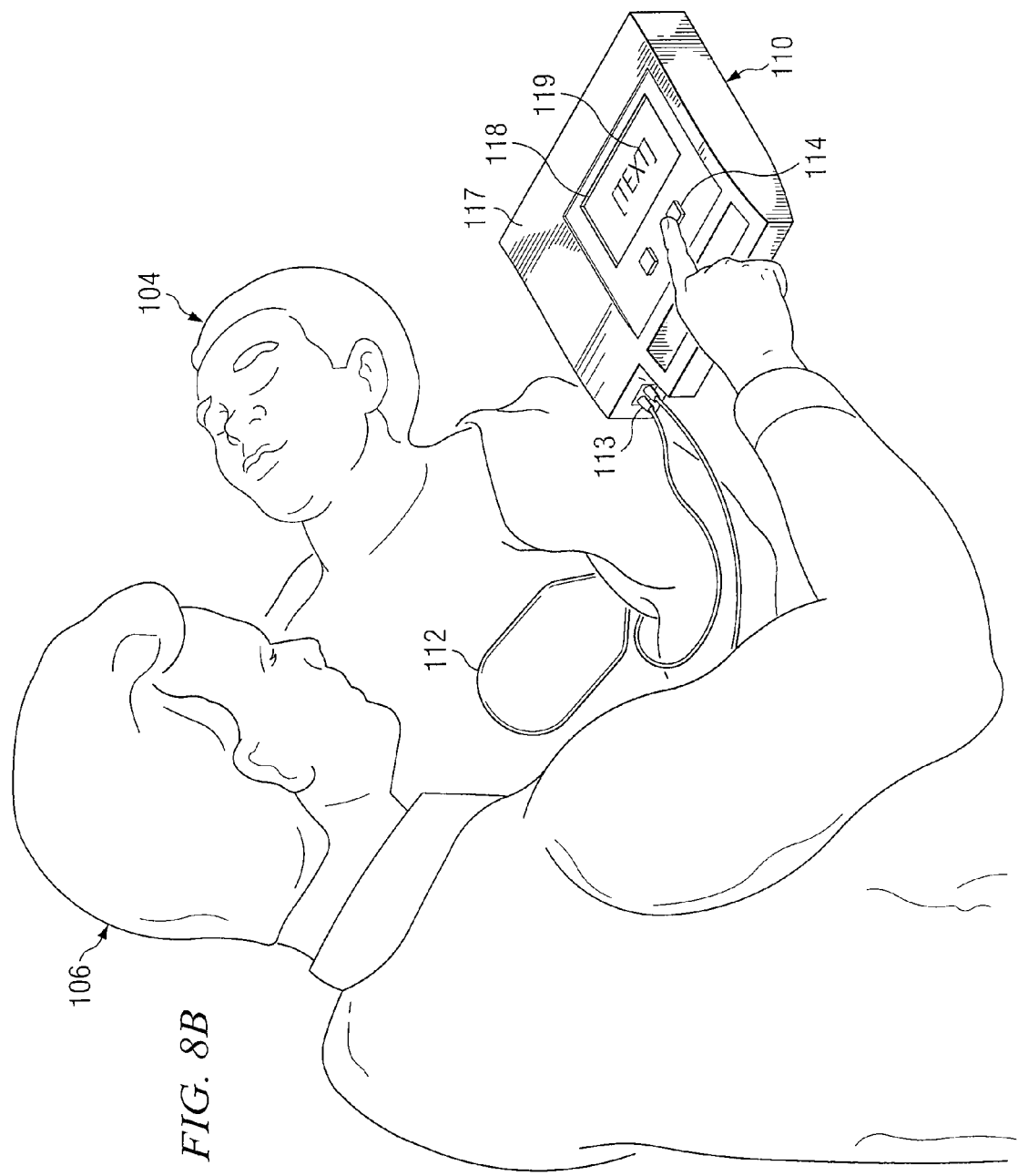

FIGS. 8A and 8B show one method for treating patient 104 in accordance with teachings of the present disclosure. At step 1, shown in FIG. 8A, user 106 may determine that patient 104 is the subject of an unknown medical condition that may include a cardiac condition. User 106 may further dispose AED 110 proximate to patient 104. User may further operate latch 108 to open the lid of AED 110. Latch 108 may include any device operable to provide access to working portions of AED 110.

At step 2, shown in FIG. 8A, user 106 may read or otherwise follow directions or instructions 119 provided by AED 110. Instructions 119 may include any elements of a treatment protocol, such as ACLS protocol, and/or other instructions preparatory to delivering treatment. For example, in embodiments such as that shown in FIGS. 8A and 8B, instructions 119 may include directives to remove the portion of patient's 104 clothing over his/her chest. In other embodiments, instructions 119 may include directives to check patient 104 for responsiveness, a carotid pulse, or other indicator of the medical condition of patient 104. In some embodiments, instructions 119 may include directives to make contact with Emergency Medical Services or other personnel. In embodiments such as that shown in FIG. 8A and 8B, instructions 119 may include directives to prepare and place electrodes 112 in appropriate locations relative to patient 104.

At Step 3, shown in FIG. 8B, AED 110 may have completed analysis of cardiac indicators of patient 104. Such indicators may include, but are not limited to, blood pressure, heart rhythms, and/or any other measurable quantity or quality related to the cardiac system of patient 104. AED 110 may collect relevant data through electrodes 112, shown in FIG. 8B as attached to the chest of patient 104 via leads 113. In other embodiments, AED 110 may collect relevant data through any combination of sensors operable to deliver a signal to AED 110.

AED 110, as discussed in relation to FIG. 7, may include a display or other component intended to communicate instructions 119 to user 106. In embodiments such as that shown in FIG. 8B, AED 110 may include a sound recording instructing user 106 to activate a shock to defibrillate patient's 104 heart. User 106 may comply with that instruction by pressing button 114, or any other actuator or switch provided by AED 110.

AED 110 may also provide additional directives, such as an instruction to ensure no one is in physical contact with patient 104.

Figure 9A:
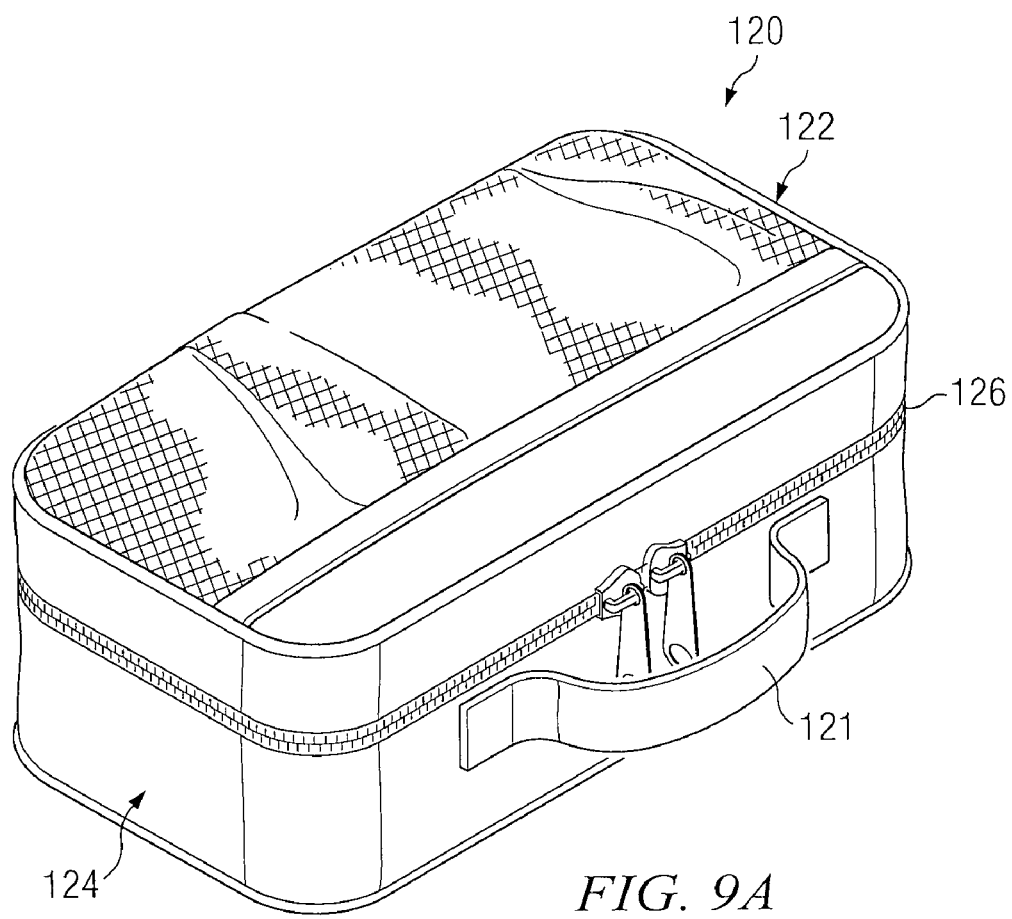
FIG. 9A is a schematic drawing showing an embodiment of an intraosseous device installation kit in accordance with teachings of the present disclosure.
Figure 9B:
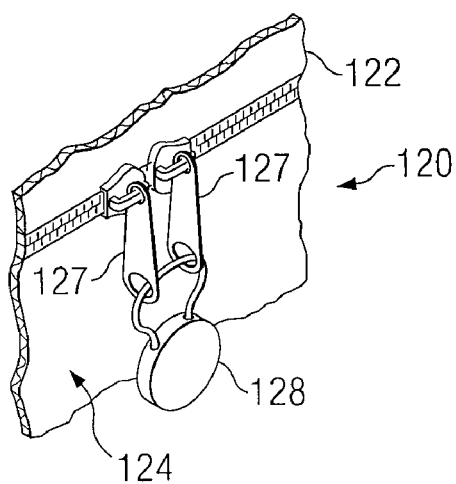
FIG. 9B is a schematic drawing showing a close-up view of a portion of an intraosseous device installation kit as depicted in FIG. 9A.

FIG. 9A illustrates one example of an intraosseous device placement kit 120 in accordance with teachings of the current disclosure. FIG. 9B shows a close-up of one feature that might be included in embodiments such as that shown in FIG. 9A. Kit 120 may include a case and/or bag configured to house and/or transport implements, tools, and/or other material that might be useful in placing an IO device in accordance with teachings of the present disclosure. In embodiments such as that shown in FIG. 9A, kit 120 may include first side 122, second side 124, handle 121, and zipper 126.

Handle 121 may include any device, feature or characteristic of kit 120 configured to facilitate grasping or manipulation of kit 120 by user 106. For example, handle 121 may include a depression in the body of kit 120 configured to fit user's 106 hand or fingers, a separate piece of material attached to the body of kit 120, or an extension of some part of the body of kit 120. In examples such as that shown in FIG. 9A, handle 121 may include a rugged piece of material (e.g., fabric, plastic, metal, and/or any other suitable material) attached to second side 124 of kit 120.

Kit 120 may include first side 122 and second side 124 configured to contain and/or protect the components within kit 120. Kit 120 may also include any combination configured to allow user 106 to access the components within kit 120. For example, in embodiments such as that shown in FIG. 9A, kit 120 may include a generally block-shaped box with first side 122 including some fraction of the total box and second side 124 including the remaining portion of the total box. The interior volume of each side may be configured to house the components within kit 120. At the same time, the separation of first side 122 from second side 124 may allow user 106 to access the components.

Zipper 126 may include any component or device configured to releasably join first side 122 with second side 124. Zipper 126 may include features or designs configured to interact with user's 104 fingers or hands to facilitate the user 104 opening kit 120. In embodiments such as that shown in FIG. 9A, opening kit 120 may consist of operating zipper 126 to allow separation of first side 122 from second side 124. In such embodiments, zipper 126 may include pulls 127, tabs or other components configured to facilitate the operation of zipper 126. In other embodiments, opening kit 120 may consist of operating any sort of connector (e.g., a clasp, buckles, straps, velcro-brand hook and loop fasteners, and/or any other releasable connector).

FIG. 9B shows a close-up of one portion of kit 120. Kit 120 may include latch 128. Latch 128 may include any device or mechanism configured to restrict accidental, inadvertent or unauthorized operation of zipper 126. In embodiments such as that shown in FIG. 9B, zipper 126 may include latch 128. Latch 128 may be configured to restrict the accidental or inadvertent separation of pulls 127. In addition, latch 128 may be configured to open or release with minimal effort by user 104, such as by pulling or squeezing latch 128 (e.g., as is present in conventional devices like some keyrings, carabineers, and/or any other quick-release mechanism).

Figure 10A:
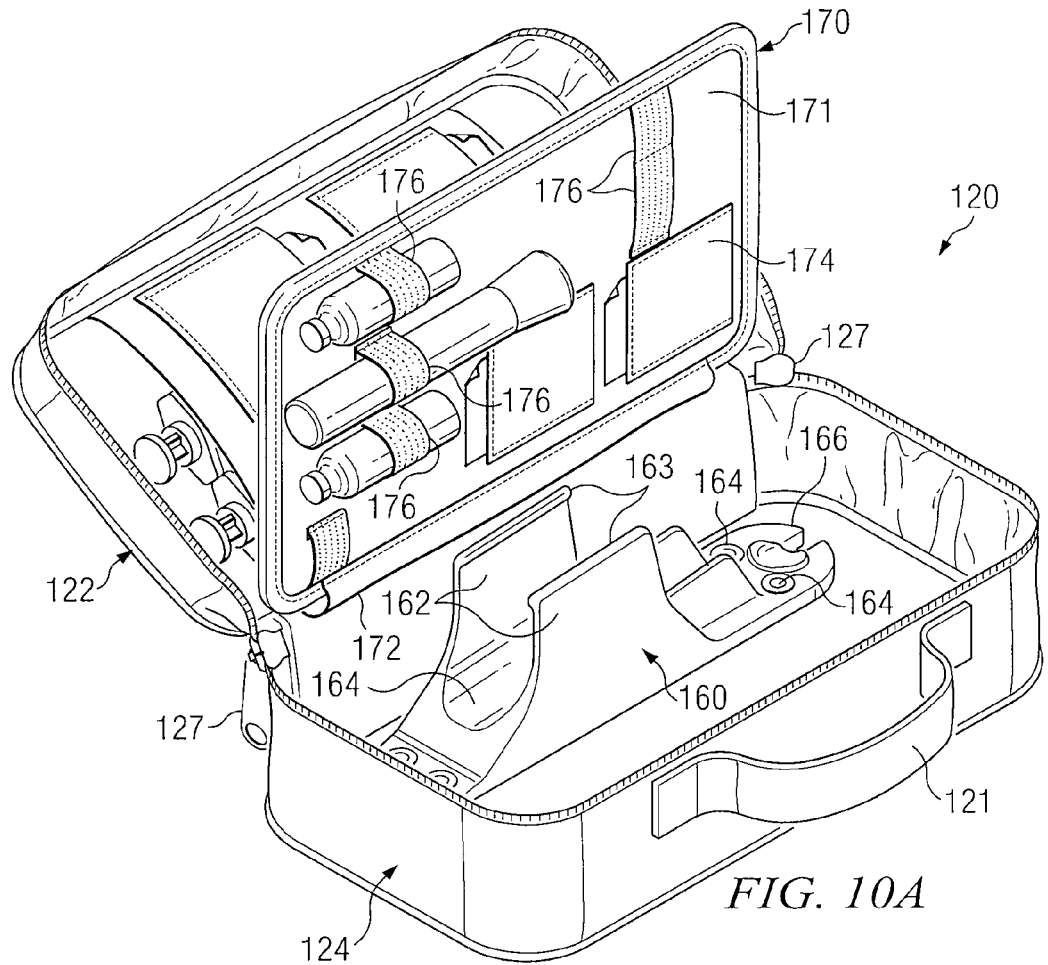
FIG. 10A is a schematic drawing showing an embodiment of an intraosseous device installation kit in accordance with teachings of the present disclosure.

FIG. 10A shows a schematic drawing of kit 120 in the open state, including interior features. Kit 120 may include IO driver bracket 160, interior partition 170, and/or assorted pockets and features configured to store or contain items useful in the installation of an intraosseous device. Persons having ordinary skill in the art will recognize that the interior of kit 120 may be configured or constructed from a wide variety of materials and in a wide variety of shapes and sizes as appropriate for the items intended to be placed in kit 120. Although the interior of kit 120 is herein described with respect to the embodiment shown in FIGS. 10A and 10B, the teachings of the present disclosure are not limited to such embodiments.

Bracket 160 may include any component or device configured to releasably store powered driver 10 or manual driver 10*a* and/or any other device configured to facilitate insertion of an intraosseous device. Bracket 160 may include extended sides 162, cradle 164, base 166, and connectors 168. Bracket 160 may be fabricated from extruded plastic, molded plastic, wood, and/or any other material suitable for forming the desired shape. In some embodiments, bracket 160 may include elastic straps, and/or any combination of straps and fasteners (e.g., Velcro, hooks, buckles, etc.).

Extended sides 162 may include any feature of bracket 160 configured to extend from the main body of bracket 160. In embodiments such as that shown in FIG. 10A, extended sides 162 may include basically planar bodies as well as lip 163 and/or other feature. Lip 163 may include any feature of extended sides 162 configured to snap on to or grip driver 10 and to withstand incidental and/or inadvertent forces applied to driver 10.

Cradle 164 may include any component or feature of bracket 160 configured to conform or otherwise interact with handle 16 of driver 10. Cradle 164 may include a shape substantially matching handle 16 for one specific driver 10 or it may include a general shape configured to interact with a wide variety of drivers 10.

Base 166 may include any component or feature of bracket 160 configured to provide attachment points between bracket 160 and the interior of kit 120. In embodiments such as that shown in FIG. 10A, bracket 160 may be fastened to second side 124. In other embodiments, bracket 160 may be attached to any other feature or part of kit 120. In addition, bracket 160 may be formed monolithically with one or more portions of kit 120 and may not include base 166 at all.

Connectors 168 may include any device or component configured to connect base 166 and/or bracket 160 to kit 120. Connectors 168 may include permanent connectors (e.g., rivets, and/or nails) or may include releasable and reusable fasteners (e.g., bolts, screws, and/or studs). In embodiments such as that shown in FIG. 10A, connectors 168 may include rivets and washers permanently fastening bracket 160 within kit 120.

Interior partition 170 may include any component or feature of kit 120 operable to segregate interior compartments of kit 120. In addition, interior partition 170 may be configured to store devices or components of an IO installation device. In embodiments such as that shown in FIG. 10A, interior partition 170 may include divider 172, flexible connector 174, pockets 176 and loops 178.

Divider 172 may include any feature or component of interior partition 170 configured to separate one interior portion of kit 120 from another. For example, divider 172 may include a sheet of sturdy flexible material. In other embodiments, divider 172 may include a rigid divider, a lid for one or more interior compartments, or similar structure.

Flexible connector 174 may include any feature or component of interior partition 170 configured to allow relative motion between interior partition 170 and kit 120. For example, flexible connector 174 may include a strip of fabric or plastic. In other examples, flexible connector 174 may include an articulate component (e.g., a hinge, clevis pin, and/or other joint).

Pockets 176 may include any feature or component of interior partition 170 configured to house or contain devices or component configured to facilitate the insertion or use of an IO device in accordance with teachings of the present disclosure. In embodiments such as that shown in FIG. 10A, pockets 176 may include portions of fabric, plastic or another material connected to interior partition 170 and configured to allow insertion and removal of devices, paper, cards, or other useful items. For example, pockets 176 may include compartments configured to allow the insertion and removal of index cards or pre-printed cards with instructions for use or other useful information.

Loops 178 may include any component or feature of interior partition 170 configured to releasably hold components of IO insertion devices or kit 120. For example, loops 178 may include strips of elastic material configured to stretch for insertion of components and retract to hold those components securely. In some embodiments, loops 178 may include fabric or plastic material. Persons having ordinary skill in the art will recognize that loops 178 and pockets 176 may be made of any size, shape and configuration appropriate to house any device or component suitable for kit 120.

Figure 10B:
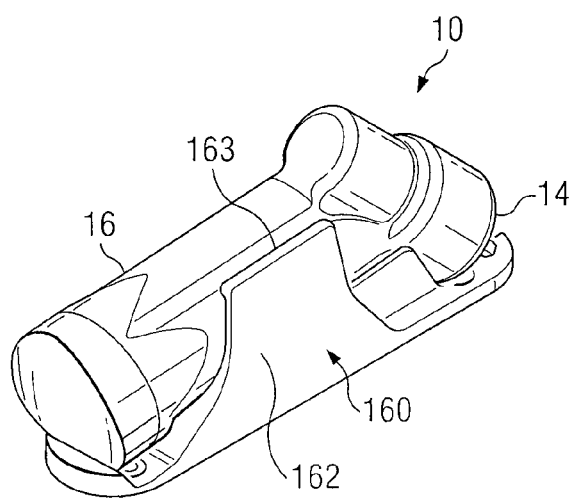
FIG. 10B is a schematic drawing showing a close-up view of a portion of an intraosseous device installation kit as depicted in FIG. 10A.

FIG. 10B shows a close-up view of bracket 160 along with driver 10. FIG. 10B depicts one embodiment of powered driver 10 present and stored within bracket 160. In embodiments such as that depicted in FIG. 10B, bracket 160 may be configured to conform closely to the shape and dimensions of powered driver 10 and specifically, to handle 16. Extended sides 162 may be configured to protrude from base 166 and enclose a significant portion of handle 16. In addition, extended sides 162 may include lips 163 configured to restrict handle 16 from separation from bracket 160. In such embodiments, lips 163 may be configured to protrude above handle 16 when driver 10 may be present in bracket 160. In other embodiments, lips 163 may be configured to interface with one or more features of handle 16 to provide a physical stop. In such embodiments, the physical resistance to motion may be configured to resist incidental or inadvertent forces but to yield easily to purposeful removal of driver 10.

Figure 11:
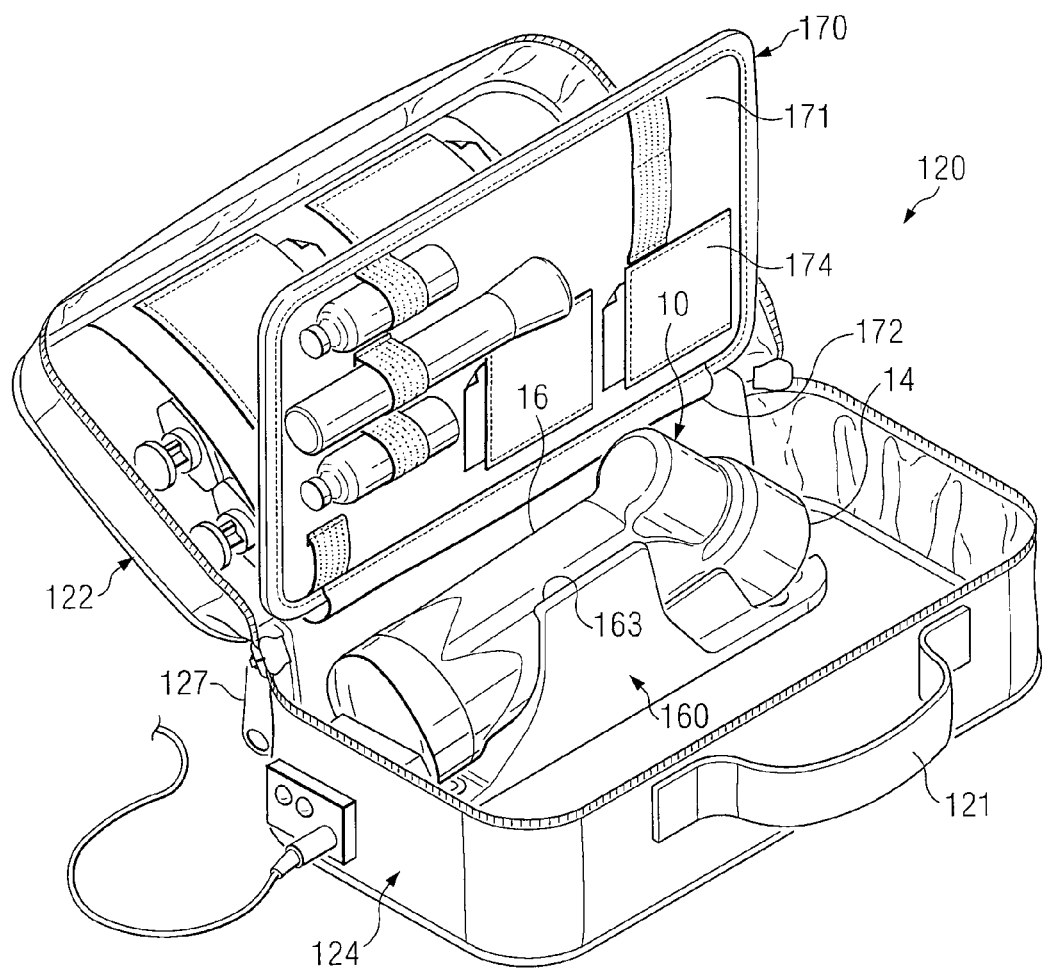
FIG. 11 is a schematic drawing showing an embodiment of an intraosseous device installation kit in accordance with teachings of the present disclosure.

FIG. 11 shows an example of kit 120 in accordance with teachings of the current disclosure, depicting driver 10 present in bracket 160. In addition, FIG. 11 depicts components configured to facilitate providing an electric charge to driver 10 while present in bracket 160. Kit 120 may include charger 180, cord 182, power indicator 184, and charging indicator 186.

Charger 180 may include any device or component configured to provide an electrical connection between an external source of electricity and driver 10. For example, charger 180 may include an AC/DC converter, electric contacts, or any other components useful in supplying power to driver 10.

Power cord 182 may include any device or component configured to connect charger 180 to an external source of power. For example, power cord 182 may include cable, wire, conductors and/or any peripheral devices useful for creating an electrical connection such as a two- or three-prong plug.

In embodiments such as that shown in FIG. 11, charger 180 may include power indicator 184 and charging indicator 186. Such indicators are well-known in applications for rechargeable household appliances such as cordless telephones, wireless shavers, and the like. In such embodiments, power indicator 184 may include an LED that emits green light when charger 180 is connected to an active power source. In such embodiments, charging indicator 186 may include an LED that emits red light when driver 10 is accumulating an electrical charge.

Figure 12:
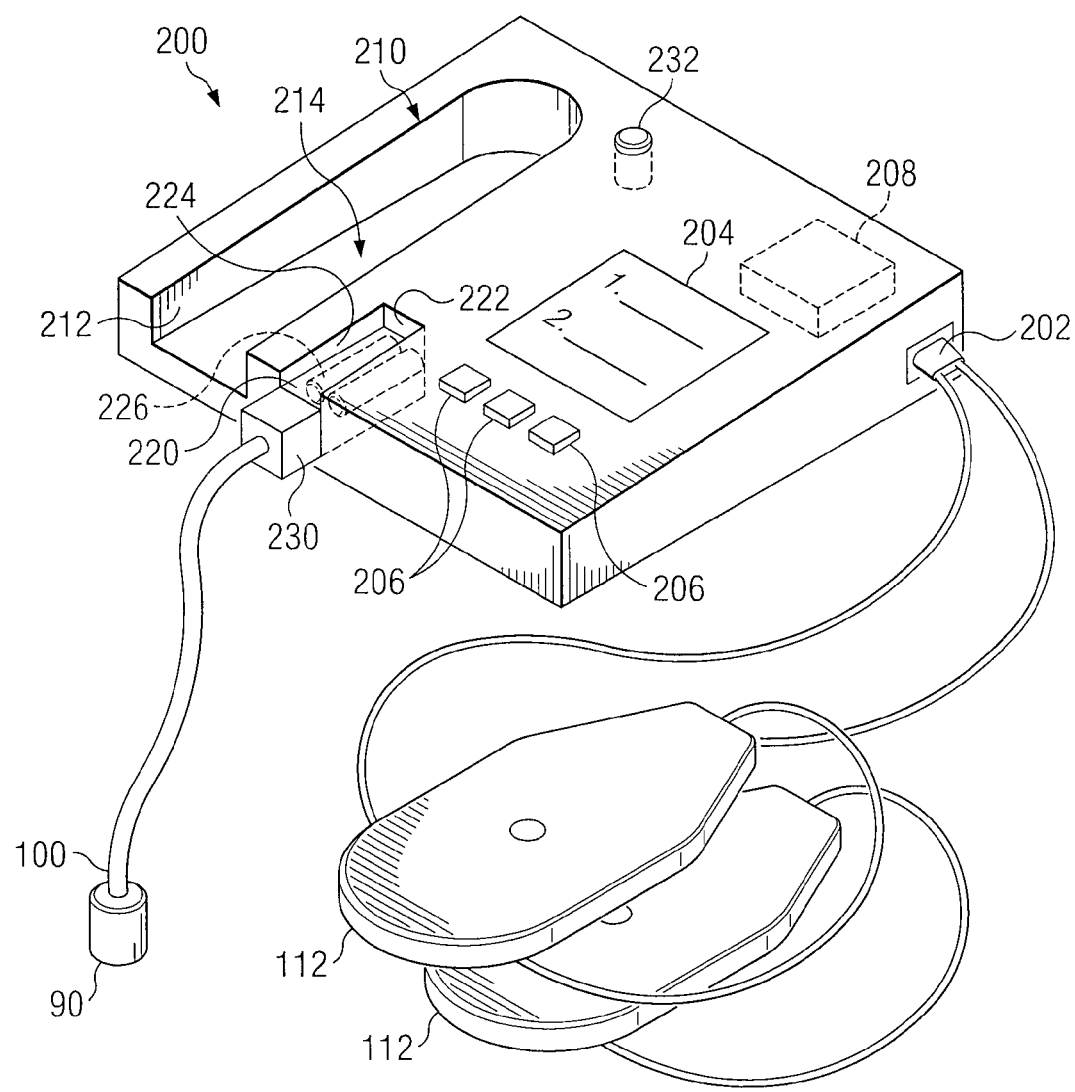
FIG. 12 is a schematic drawing showing an embodiment of a combined intraosseous device installation kit and automatic external defibrillator in accordance with teachings of the present disclosure.

FIG. 12 is a depiction of an embodiment of apparatus 200 combining AED 110 and IO installation kit 120 in accordance with teachings of the present disclosure. In such embodiments, apparatus 200 may include electrodes 112, electrode port 202, display 204, controls 206, processor 208, driver cradle 210, drug delivery slot 220, and drug delivery port 230. In other embodiments, not all of these features may be present.

Electrodes 112, as described in more detail with relation to FIG. 7, may include any device configured to releasably connect apparatus 200 with patient 104 and operable to collect cardiac information from patient 104.

Electrode port 202 may include any connector configured to connect electrodes 112 with processor 208 both physically and for the transfer of data. For example, electrode port 202 may include, e.g., a twist-on wire connector, terminals, terminal blocks, banana plugs, crimp-on terminals, lugs, plug and socket connectors, DIN connector, D-subminiature plugs, registered jack and/or any other suitable connectors.

Display 204 may include any device or component operable to communicate data or instructions to user 106. For example, display 204 may include a LCD screen or touchpad such as those used in laptop computers. In other examples, display 204 may include a plasma display, a set of LEDs, a segment display, a cathode ray tube, and/or any other useful means of displaying information. Display 204 may be operable to instruct user 106 regarding proper installation of electrodes 112, proper treatment of patient 104, and/or any other information useful in the treatment of patient 104.

Controls 206 may include any device configured to allow user 106 to operate apparatus 200. In embodiments such as that shown in FIG. 12, controls 206 may include depressible buttons. In other embodiments, controls 206 may include any similar input device (e.g., switches, touchpads, and/or dials). As example functions, controls 206 may be operable to indicate electrodes 112 have been attached to patient 104, to query processor 208, to activate a defibrillating shock, to deliver drugs or medication present in drug delivery slot 220, or any other function useful in practicing the teachings of the present disclosure.

Processor 208 may include any device or devices for processing signals received from electrodes 112 (e.g., converting analog signals to digital signals, and/or interpreting identifiers (e.g., serial numbers, device codes and/or other codes) of various components in apparatus 200). For example, processor 208 may include a device configured to receive a signal generated by electrodes 112, analyze the received signal, and/or convert the signal to a format suitable for communication to user 106. Processor 208 may include any suitable hardware or software (e.g., any suitable software, algorithms, or other logic or instructions).

Driver cradle 210 may include any feature or component of apparatus 200 configured to releasably contain driver 10 or manual driver 10a. In some embodiments, driver cradle 210 may include any features of bracket 160 discussed in relation to FIG. 10A. In other embodiments, such as that shown in FIG. 12, driver cradle 210 may include sidewalls 212 and bottom 214.

Sidewalls 212 may include any feature or component of apparatus 200 configured to releasably hold driver 10 or manual driver 10a until user 106 prepares to install an IO device. Sidewalls 212 may be configured to hold driver 10 with IO needle set 40 connected to driver 10 or without IO needle set 40 connected to driver 10. In some embodiments, such as that shown in FIG. 12, sidewalls 212 may include smooth and flat panels as in commonly available phone handset cradles.

Likewise, bottom 214 may include any configuration suitable for releasable storage of driver 10 or manual driver 10a. For example, bottom 214 may include a substantially flat, smooth portion of apparatus 200. As another example, bottom 214 may include indentions and protrusions configured to interface with features or components of driver 10 and/or manual driver 10a. In some embodiments, bottom 214 may include features or components operable to deliver an electric charge to a battery or power source within driver 10.

Drug delivery slot 220 may include any feature or component of apparatus 200 configured to receive an infusion of medication or drugs preparatory to delivery to patient 104. In some embodiments, such as that shown in FIG. 12, drug delivery slot may be configured to accept and dispense drugs stored in cartridges 226. In such embodiments, drug delivery slot 220 may include top 222 and sidewalls 224. Drug delivery slot 220 may include any features or devices configured to delivery drugs and/or medication from cartridge 226 to drug delivery port 230 and to a patient, e.g., through flexible tubing 100 and connector assembly 90 to an IO device. In some embodiments, drug delivery slot 220 may include features for accepting a plurality of cartridges 226. For example, drug delivery slot 220 may include six slots for accepting unit dose cartridges of drugs used in the practice of ACLS.

Top 222 may include any feature or component of drug delivery slot 220 configured to adapt to cartridge 226. For example, top 222 may include devices configured hold cartridge 226 by operating in a similar manner as a battery retainer in a conventional handheld electronic device. In other embodiments, top 222 may include a flexible protrusion configured to create a friction fit with cartridge 226, an extension configured to protrude above cartridge 226 when cartridge 226 is present in drug delivery slot 220, or any other feature configured to hold cartridge 226 in place until user 106 desires to remove cartridge 226.

Sidewalls 224 may include any feature or component of drug delivery slot 220 configured to adapt to cartridge 226. For example, sidewalls 224 may include devices configured hold cartridge 226 by operating in a similar manner as a battery retainer in a conventional handheld electronic device. In other embodiments, sidewalls 224 may include a flexible protrusion configured to create a friction fit with cartridge 226, an extension configured to protrude above cartridge 226 when cartridge 226 is present in drug delivery slot 220, or any other feature configured to hold cartridge 226 in place until user 106 desires to remove cartridge 226.

Storage slots 232 may include any feature or component of apparatus 200 configured to releasably hold cartridge 226. For example, storage slot 232 may include a cylindrical socket in the body of apparatus 200 shaped to provide a snug fit around cartridge 226. In some embodiments, storage slots 232 may be located in the side, top, or bottom of apparatus 200. In other embodiments, cartridges 226 may be stored in kit 120 or pockets 174 and loops 176 associated with apparatus 200.

In other embodiments, drug delivery slot may be configured to receive drugs without interface with cartridge 226. For example, drug delivery slot 220 may include a rubber gasket suitable for puncture by a hypodermic needle.

Drug delivery port 230 may include any feature or component of apparatus 200 configured to provide an interface between drug delivery slot 220 and flexible tubing 100 and connector assembly 90 (discussed in relation to FIGS. 5 and 6). For example, drug delivery port 230 may include a luer lock connection. Drug delivery port 230 may include any other appropriate joint (e.g., a valve, a threaded fitting, a plug and socket, and/or any component appropriate to provide a fluid connection between apparatus 200 and patient 104).

Figure 13A:
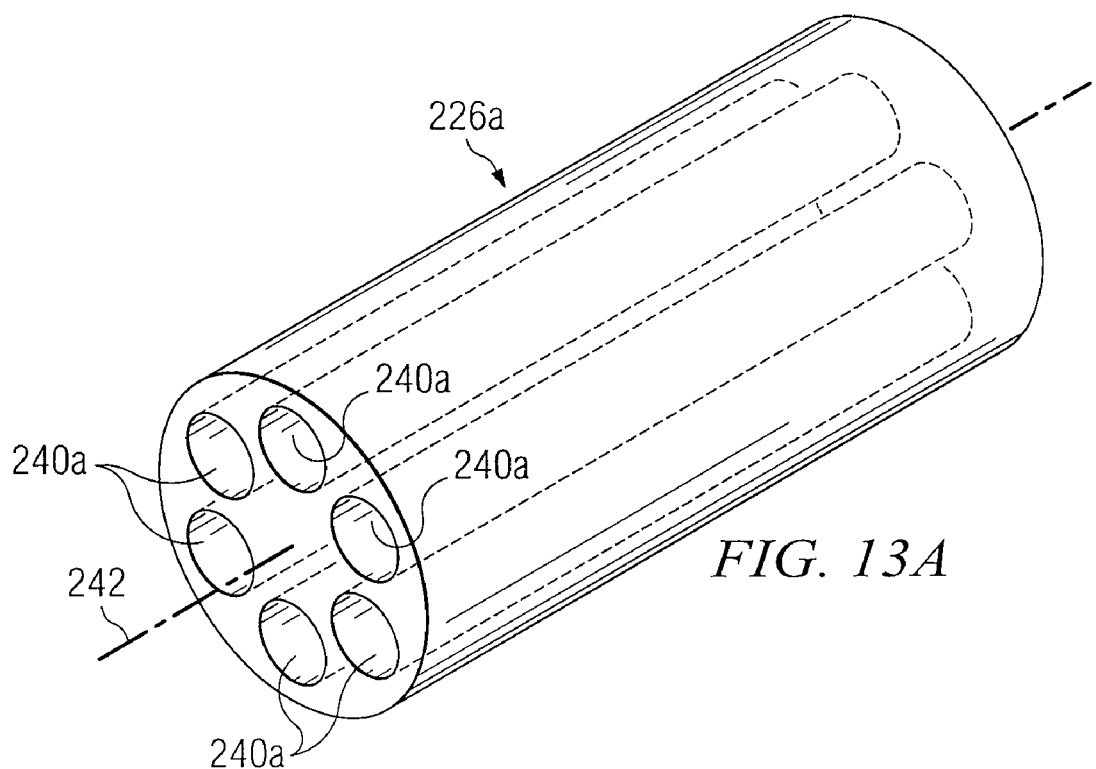
FIGS. 13A and 13B are schematic drawings showing respective embodiments of a drug cartridge for use in accordance with teachings of the present disclosure.
Figure 13B:
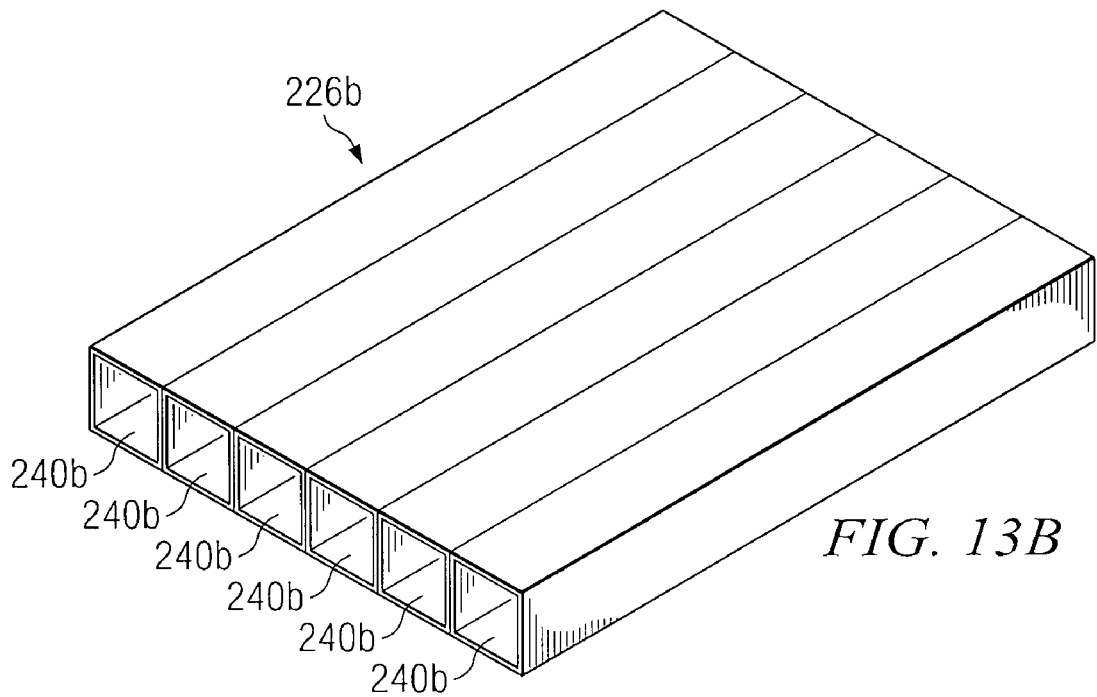

FIGS. 13A and 13B show examples of cartridges which may be used with medical apparatus incorporating teachings of the present disclosure. Cartridges 226a and 226b may include any device configured to store a medication or drug and interface with apparatus 200. Cartridges 226a and 226b may be configured to fit in storage slots 232 as well as drug delivery slot 220. Cartridges 226a and 226b may include a canister, a vial, a syringe, and/or any other pre-filled sterile container appropriate for the storage of medications and/or drugs. In some embodiments, cartridges 226a and 226b may include a known single unit dose drug cartridge. In some embodiments, cartridges 226a and 226b may include a marker identifying the contents of cartridges 226a and 226b (e.g., color-coding, text, chemical formulations, and/or any other information that may be used to indicate the contents of cartridges 226a and 226b to a user).

In other embodiments, such as those shown in FIGS. 13A and 13B, cartridges 226a and 226b may include multiple chambers 240a and 240b. In such embodiments, each chamber may be configured to hold a single dose of a medicine, drug, and/or a flushing solution. In such embodiments, drug delivery slot 220 may include any features and/or devices configured to select a chamber, provide a fluid connection between the chamber and drug delivery port 230, deliver fluid from the chamber to drug delivery port 230 and then to a patient (e.g., via flexible tubing 100, connector assembly 90 and an IO device). Those embodiments of cartridges 226a and 226b with multiple chambers may include a rotating component that alternates drug chambers with chambers filled with sterile solutions. In such embodiments, drug delivery slot 220 may inject fluid from the chambers filled with sterile solution after injecting fluid from a drug chamber to flush drug delivery port 230, flexible tubing 100, connector assembly 90, and/or an IO device.

As shown in FIG. 13A, cartridge 226a may have a generally cylindrical configuration with rigid walls. Chambers 240a may be disposed around a central axis 242. In such embodiments, each chamber 240a may be filled with a single dose of a drug, medication, and/or sterile flushing fluid. In such embodiments, drug delivery slot 220 may include any necessary components or features configured to deliver the contents of each chamber 240a and to rotate cartridge 226a around axis 242 as needed to access each chamber 240a.

FIG. 13B shows another embodiment of cartridge 226b including multiple chambers 240b. Cartridge 226b may have a generally rectangular configuration with relatively rigid walls. Alternatively, cartridge 226b may be formed from relatively flexible material to accommodate storage, insertion, and removal from an associated medical device and/or apparatus.

Cartridge 226 may include one or more chambers 240b disposed along the length of cartridge 226. In such embodiments, each chamber 240b may be filled with a single unit dose of drug, medication and/or sterile flushing solution. In such embodiments, drug delivery slot 220 may include any necessary components or features configured to deliver the contents of each chamber 240b as needed by apparatus 200.

Figure 14:
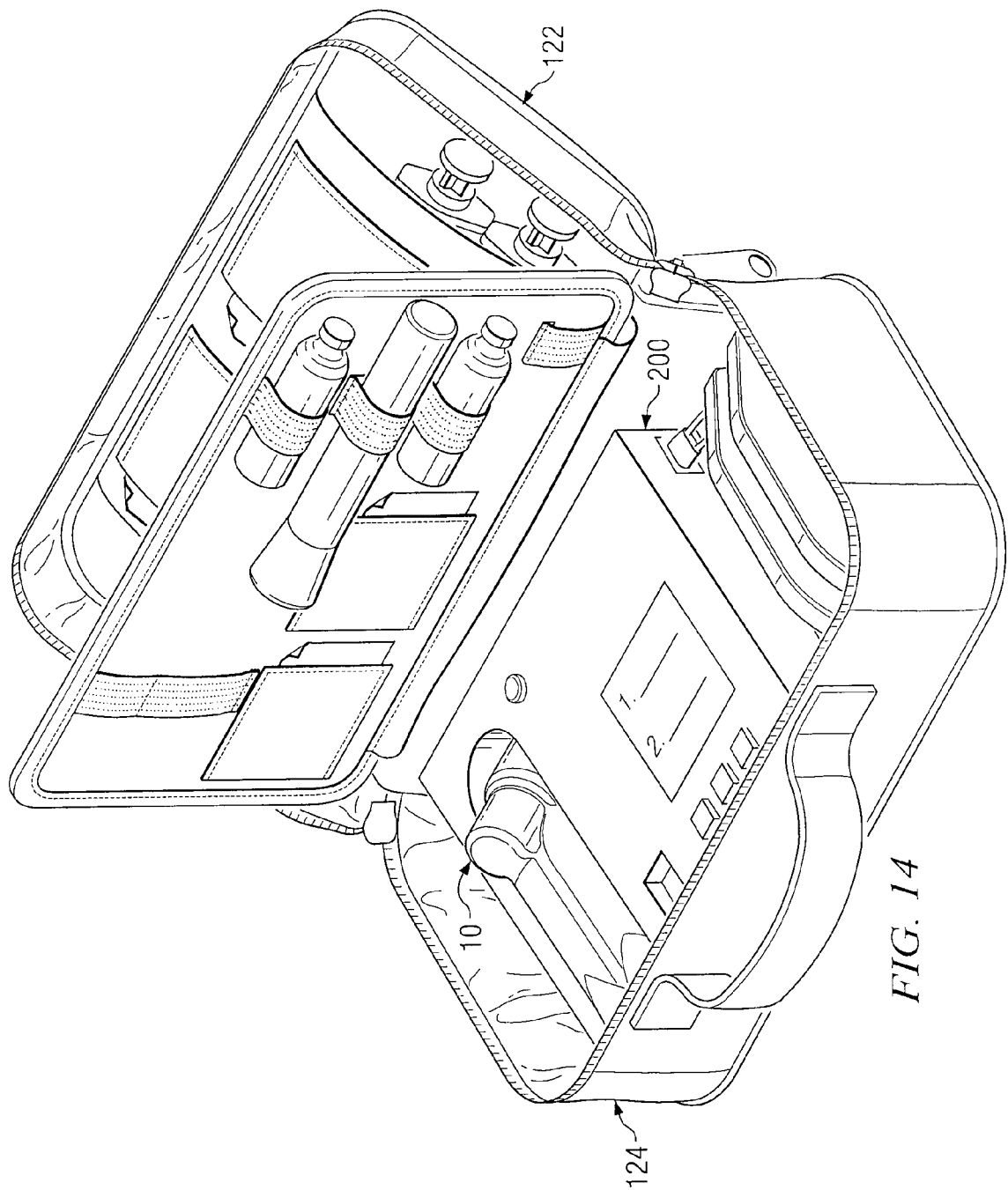
FIG. 14 a schematic drawing showing an embodiment of a combined intraosseous device installation kit and automatic external defibrillator in accordance with teachings of the present disclosure.

FIG. 14 depicts one embodiment of apparatus 200 in accordance with teachings of the present disclosure. In embodiments such as that shown in FIG. 12, apparatus 200 may include the features previously discussed in relation to kit 120 and AED 110. Such embodiments may include driver 10, electrodes 112, interior partition 170, charger 180, electrode port 202, display 204, controls 206, processor 208, driver cradle 210, drug delivery slot 220, and drug delivery port 230. Such embodiments may provide a single kit operable to perform the functions previously described in relation to AED 110 and kit 120.

Figure 15:
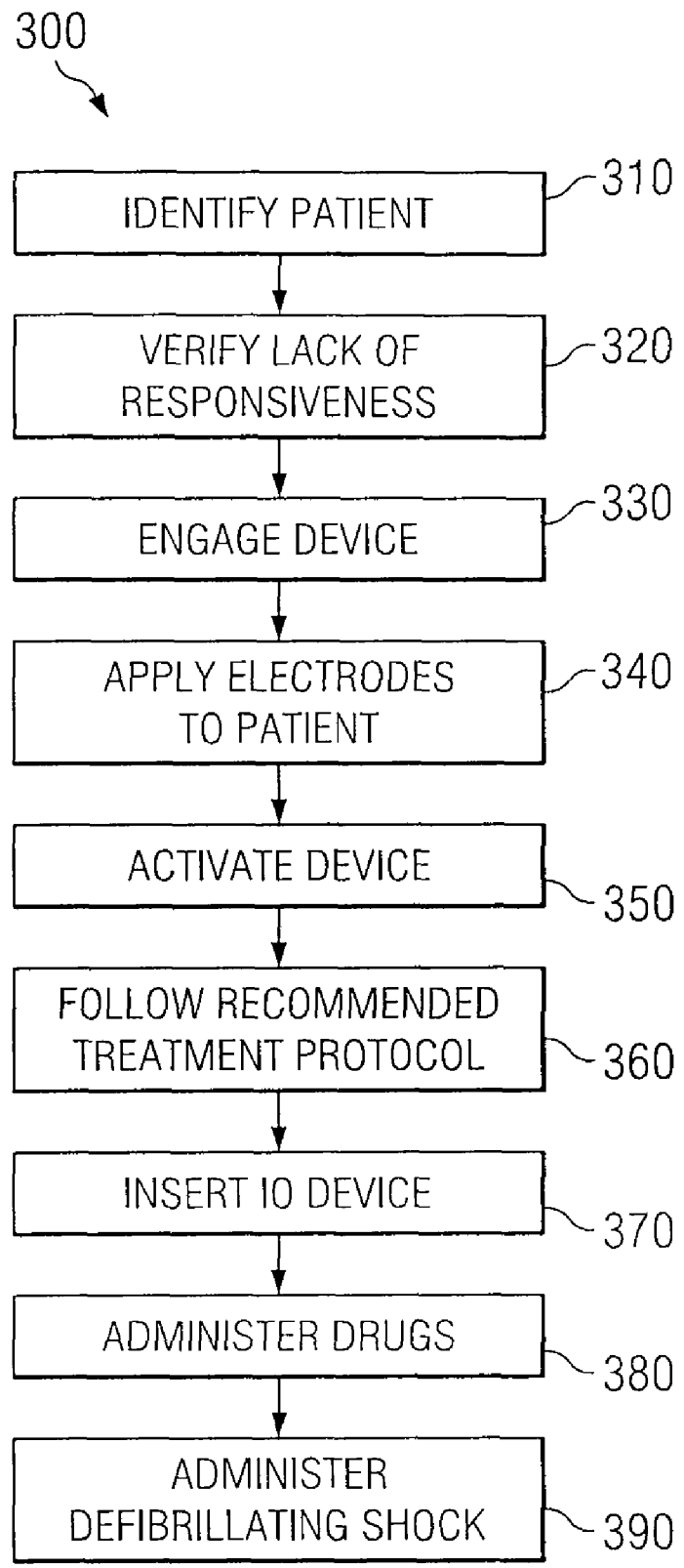
FIG. 15 is a flowchart showing a method of treating a patient in accordance with teachings of the present disclosure.

FIG. 15 shows a flowchart depicting a method 300 of treating patient 104 by user 106 including apparatus 200, a combination AED and IO drug delivery kit, in accordance with teachings of the present disclosure. At step 310 patient 104 may be identified, which may include recognizing physical signs of distress, hearing a call for help, responding to a call for emergency services, or any other process capable of identifying patient 104.

At step 320, the lack of responsiveness of patient 104 may be confirmed. Step 320 may include performing preliminary diagnosis, asking questions, receiving information from witnesses and/or bystanders, and/or any other suitable procedure intended to confirm the condition of patient 104.

At step 330, apparatus 200 may be engaged for the treatment of patient 104. Engagement of apparatus 200 may include opening apparatus 200 to expose display 204, controls 206 and/or instructions. Engagement of apparatus 200 may be retrieved from a wall-mount, an emergency vehicle, a supply of medical equipment, and/or any other storage facility or transport equipment suitable for carrying or storing apparatus 200. Engagement of apparatus 200 may include following any directions or instructions included with apparatus 200 or provided by display 204.

At step 340, electrodes 112 may be applied to patient 104. Application of electrodes 112 may include removal of clothing or other obstacles to the chest of patient 104. Application of electrodes 112 may include releasably connecting electrodes 112 to appropriate portions of patient's 104 skin.

At step 350, apparatus 200 may be activated. In some embodiments, activation of apparatus 200 may include operation of controls 206. In other embodiments, activation of apparatus 200 may include apparatus 200 sensing that electrodes 112 are in place and automatically engaging in analysis of any data gathered. Activation of apparatus 200 may include switching apparatus 200 on and/or any other method of activating the power circuitry of apparatus 200.

At step 360, a recommended treatment protocol may be followed. In some embodiments, recommended treatment protocol may include ACLS treatment protocol for cardiac arrhythmia. Following a recommended treatment protocol may include responding to directions or instructions provided by apparatus 200, communicated on display 204, and/or any other method of instructing user 106.

At step 370, IO needle set 40 may be inserted into the vascular system of patient 104. Insertion of IO needle set 40 may be a part of instructions or directions provided by apparatus 200. Insertion of IO needle set 40 at step 370 may include the use of any of the IO insertion components discussed in the present disclosure. Insertion of IO needle set 40 may include connecting apparatus 200 to flexible tubing 100 via drug delivery port 230 or any other component providing access to the vascular system of patient 104.

At step 380, drugs or medication may be administered to patient 104. Administration of drugs may be as a response to instructions or directions provided by apparatus 200. Administration of drugs may include insertion of cartridge 226 into drug delivery slot 220 and/or any other means of communicating drugs from apparatus 200 to patient 104. Administration of drugs may be accomplished by user 106 activation of control 206 or may include an automatic function of apparatus 200 upon analysis of data collected via electrodes 112. In some embodiments, apparatus 200 may administer drugs without user interaction, e.g., automatically delivering drugs from a multi-chamber drug cartridge 226. In such embodiments, apparatus 200 may administer a first drug from one chamber followed by a flushing solution from a second chamber of cartridge 226.

At step 390, defibrillating shock may be administered to patient 104. Administration of defibrillating shock may be as a response to instructions or directions provided by apparatus 200. Administration of defibrillating shock may be accomplished by user 106 activation of control 206 or may include an automatic function of apparatus 200 upon analysis of data collected via electrodes 112.

Although the present disclosure and its advantages have been described in relation to intraosseous devices, it should be clear to a person having ordinary skill in the art that these teachings can be applied to support a variety of medical devices in relation to a patient. For example, embodiments of the present disclosure might be utilized to provide fluid to any intravenous connection or device, a central line, an endotracheal tube, a chest tube, a catheter, dialysis tubing and/or any other device intended to make a fluid connection to one or more systems of the patient.

Examples of acute and chronic conditions which may be treated using intraosseous devices and procedures incorporating teachings of the present disclosure include, but are not limited to, the following:

Anaphylaxis (epinephrine, steroids, antihistamines, fluids, and life support)

Arrhythmia (anti-arrhythmics, electrolyte balance, life support);

Burns (fluid replacement, antibiotics, morphine for pain control);

Cardiac arrest (epinephrine, atropine, amiodarone, calcium, xylocaine, magnesium);

Congestive heart failure (life support, diuretics, morphine, nitroglycerin);

Dehydration (emergency port for life support, antibiotics, blood, electrolytes);

Diabetic Ketoacidosis (life support, electrolyte control, fluid replacement);

Dialysis (emergency port for life support, antibiotics, blood, electrolytes);

Drug overdose (naloxone, life support, electrolyte correction);

Emphysema (life support, beta adrenergics, steroids);

Hemophiliacs (life support, blood, fibrin products, analgesics);

Osteomyelitis (antibiotics directly into the site of infection, analgesics);

Pediatric applications (shock, dehydration, nutrition, electrolyte correction);

Seizures (anti-seizure medications, life support, fluid balance);

Shock (life support fluids, pressor agents, antibiotics, steroids);

Sickle cell crisis (fluid, morphine for pain, blood, antibiotics, exchange transfusion);

Trauma (emergency port for life support fluids, antibiotics, blood, electrolytes);

Although the present disclosure and its advantages have been described in detail, it should be understood that various changes, substitutions and alternations can be made herein without departing from the spirit and scope of the disclosure as defined by the following claims.

What is claimed is:

1. Medical apparatus for treating a patient comprising:
two electrodes, the two electrodes including an attachment operable to releasably connect the two electrodes to the patient;
a processor operable to collect and analyze a rhythm associated with the patient's heart from the two electrodes;
a display operable to communicate instructions to a user;

an intraosseous device and a driver operable to insert the intraosseous device into a bone and associated bone marrow of the patient;

a drug delivery slot having at least one dose of a drug disposed therein;

a drug delivery port operable to communicate the drug from the drug delivery slot to the patient via the intraosseous device; and a voltage source operable to deliver an electric shock to the patient via the two electrodes; and a housing configured to house the processor, the display, the drug delivery slot, the drug delivery port and the voltage source.

2. The medical apparatus of claim 1 further comprising:
the processor operable to analyze the rhythm based on the Advanced Cardiac Life Support protocol; and
the drug delivery port operable to communicate the drug as prescribed based on the Advanced Cardiac Life Support protocol.

3. The medical apparatus of claim 1 further comprising a rechargeable power supply operable to energize the processor, the display, and the voltage source.

4. The medical apparatus of claim 1 wherein the driver comprises a battery power supply.

5. The medical apparatus of claim 1 comprising the processor operable to activate the voltage source.

6. The medical apparatus of claim 1 wherein the housing further comprises a cradle configured to releasably hold the driver.

7. The medical apparatus of claim 1 wherein the housing further comprises one or more storage slots configured to releasably hold a drug container.

8. The medical apparatus of claim 1 further comprising:
the driver including a rechargeable power supply; and
the housing including a charger operable to supply power to the rechargeable power supply.

9. The medical apparatus of claim 1 further comprising the drug delivery slot operable to receive a drug cartridge comprising at least two single unit dose chambers.

10. The medical apparatus of claim 9 further comprising the drug delivery slot operable to receive a drug cartridge comprising at least two single unit dose chambers surrounding a central axis.

11. Medical apparatus for treatment of a patient, the apparatus comprising:

an intraosseous device operable to penetrate a bone and associated bone marrow;

a cartridge including multiple chambers operable to hold a single dose of one or more drugs;

a drug delivery port operable to communicate the one or more drugs from the multiple chambers in the cartridge to the patient via the intraosseous device;

a processor operable to collect and analyze a rhythm associated with the patient's heart;

a display operable to communicate one or more instructions to a user in relation to treatment of the patient;

a voltage source operable to deliver a defibrillating shock to the patient; and one or more instructions with directions to administer the one or more drugs to the patient via the intraosseous device.

12. The apparatus of claim 11 further comprising two electrodes operable to communicate the rhythm to the processor.

13. The apparatus of claim 11 further comprising the processor operable to activate the voltage source.

14. The apparatus of claim 11 wherein the one or more instructions include elements of Advanced Cardiac Life Support protocol.

15. The apparatus of claim 11 wherein:
the cartridge comprises a cylindrical drug cartridge having a longitudinal axis and at least two single unit dose chambers disposed generally parallel to the longitudinal axis such that each single unit dose chamber may be accessed by rotating the cartridge around the longitudinal axis; and
each unit dose chamber is operable to communicate with the intraosseous device via the drug delivery port after the unit dose chamber has been accessed by rotating the cartridge.

16. The apparatus of claim 15 further comprising at least six single unit dose chambers disposed generally parallel to the longitudinal axis.

17. A method for treating a patient comprising:
disposing two electrodes on the chest of the patient;
activating an apparatus operable to collect and analyze a rhythm associated with the patient's heart;
receiving one or more instructions from the apparatus;
inserting an intraosseous device into the patient's vascular system in response to the one or more instructions;
automatically, without user interaction, administering a drug to the patient via the intraosseous device in response to the one or more instructions; and
administering a defibrillating shock to the patient in response to the one or more instructions.

18. The method of claim 17 wherein the apparatus provides the one or more instructions based on Advanced Cardiac Life Support protocol.

19. The method of claim 17 wherein the apparatus comprises a voltage source operable to administer the defibrillating shock via the two electrodes.

20. The method of claim 17 wherein the method further comprises connecting the intraosseous device to a drug delivery port associated with the apparatus.

21. The method of claim 17 wherein the method further comprises administering a defibrillating shock to the patient after administering a drug to the patient.

\* \* \* \* \*